United States Patent [19]

Sato et al.

[11] Patent Number: 4,970,207

[45] Date of Patent: Nov. 13, 1990

[54] BENZODIAZEPINE DERIVATIVES

[75] Inventors: Yoshinari Sato, Takaishi; Teruaki Matuo, Osaka, both of Japan

[73] Assignee: Fujisawa Pharmaceutical Company, Ltd., Osaka, Japan

[21] Appl. No.: 373,171

[22] Filed: Jun. 29, 1989

[30] Foreign Application Priority Data

Jul. 7, 1988 [GB] United Kingdom ............. 8816207.8
Aug. 31, 1988 [GB] United Kingdom ............. 8820560.4
Oct. 7, 1988 [GB] United Kingdom ............. 8823660.9

[51] Int. Cl.$^5$ ..................... A61K 31/55; C07D 703/06
[52] U.S. Cl. ..................................... 514/211; 540/509
[58] Field of Search ......................... 540/509; 514/211

[56] References Cited

U.S. PATENT DOCUMENTS 4,628,084 12/1986 Bock et al. ........................... 490/509
4,820,834 4/1989 Evans et al. ........................ 540/409

FOREIGN PATENT DOCUMENTS 167919 1/1986 European Pat. Off. ............ 540/509

*Primary Examiner*—Robert T. Bond
*Attorney, Agent, or Firm*—Oblon, Spivak, McClelland, Maier & Neustadt

[57] ABSTRACT

This invention relates to new benzodiazepine derivatives and pharmaceutically acceptable salts thereof. More particularly, it relates to new benzodiazepine derivatives and pharmaceutically acceptable salts thereof which are cholecystokinin (CCK) antagonists and therefore can be used as therapeutical agents for emesis, pancreatitis, satiety and appetite control, pain control, insulinoma, gastroparesis, acute obstructive cholecystitis, irritable bowel disease, carcinoma of pancreas, etc.

5 Claims, No Drawings

BENZODIAZEPINE DERIVATIVES

This invention relates to new benzodiazepine derivatives and pharmaceutically acceptable salts thereof.

More particularly, it relates to new benzodiazepine derivatives and pharmaceutically acceptable salts thereof which are cholecystokinin (CCK) antagonists and therefore can be used as therapeutical agents for emesis, pancreatitis, satiety and appetite control, pain control, insulinoma, gastroparesis, acute obstructive cholecystitis, irritable bowel disease, carcinoma of pancreas, etc.

The benzodiazepine derivatives of this invention can be represented by the following formula (I):

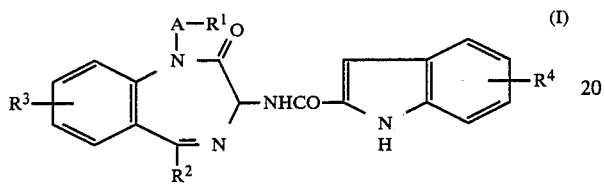

wherein $R^1$ is halogen, heterocyclic group which may have one or more suitable substituent(s), aryl which may have one or more suitable substituent(s), —NH—$R^5$ (in which is hydrogen, lower alkanoyl or hydroxy(lower)alkyl), —S—$R^6$ (in which $R^6$ is lower alkyl, lower alkyl substituted with carboxy and amino, lower alkyl substituted with protected carboxy and protected amino, or pyridyl), —O—$R^7$ (in which $R^7$ is hydrogen, hydroxy protective group, lower alkyl, lower alkenyl, ar(lower)alkyl, halo(lower)alkyl, amino(lower)alkyl, protected amino(lower)alkyl, or piperazinyl(lower)alkyl which may have lower alkyl), —CONH—$R^8$ (in which $R^8$ is cyano, carbamoyl(lower)alkyl, carboxy(lower)alkyl, protected carboxy(lower)alkyl, or lower alkyl substituted with carbamoyl and aryl), or —Z—$R^9$ [in which $R^9$ is hydrogen or lower alkyl, and Z is

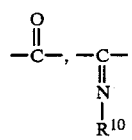

(wherein $R^{10}$ is hydroxy, lower alkoxy or amino) or

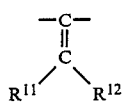

wherein $R^{11}$ is carboxy or protected carboxy and $R^{12}$ is hydrogen; or $R^{11}$ is halogen and $R^{12}$ is halogen)], $R^2$ is aryl which may have one or more suitable substituent(s), $R^3$ is hydrogen or halogen, $R^4$ is hydrogen, halogen or lower alkoxy and A is lower alkylene.

According to the present invention, the new benzodiazepine derivatives (I) can be prepared by the processes which are illustrated in the following scheme.

Process 1

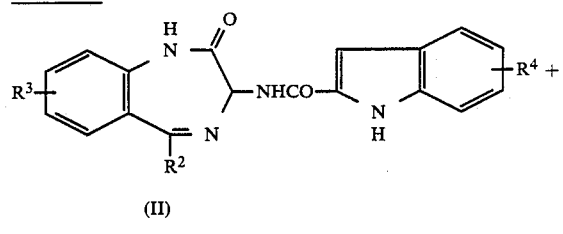

(II)

or a salt thereof

(III)

or a salt thereof

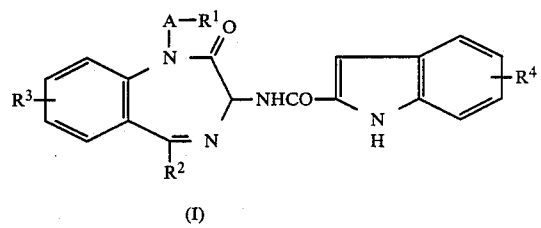

(I)

or a salt thereof

Process 2

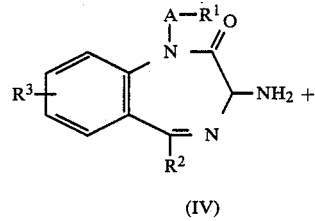

(IV)

or its reactive derivative
at the amino group
or a salt thereof

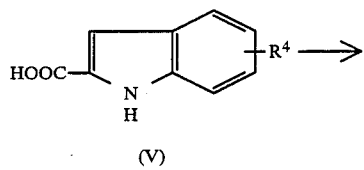

(V)

or its reactive derivative
at the carboxy group
or a salt thereof

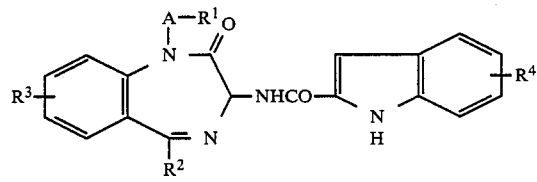

(I)

or a salt thereof

Process 3

-continued (Ia) or a salt thereof

↓ Elimination reaction of the hydroxy protective group (Ib) or a salt thereof

Process 4

(Ic) or a salt thereof

↓ Oxidation (Id) or a salt thereof

Process 5

(Ie) or a salt thereof

-continued $$(R^{13})_3 P = C \overset{R^{11}}{\underset{R^{12}}{}} \quad \longrightarrow$$

(X) or a salt thereof (If) or a salt thereof

Process 6

(Ie) or a salt thereof $R^{10}-NH_2 \longrightarrow$ (XI) or a salt thereof (Ig) or a salt thereof Process 7

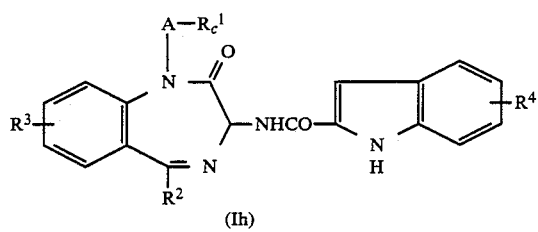

(Ih)

or a salt thereof

↓ Elimination reaction of the amino protective group

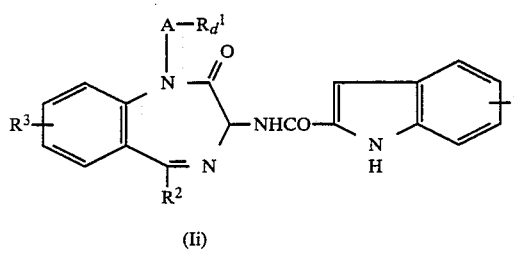

(Ii)

or a salt thereof

Process 8

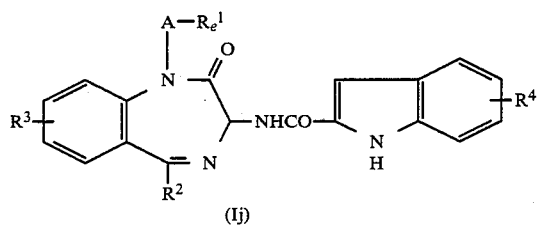

(Ij)

or a salt thereof

↓ Elimination reaction of the carboxy protective group

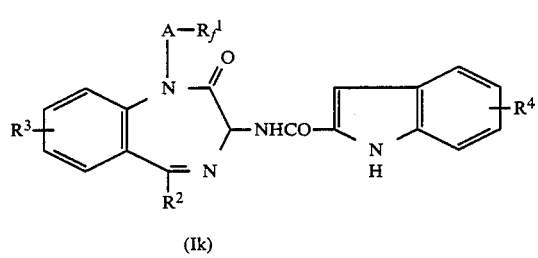

(Ik)

or a salt thereof

Process 9

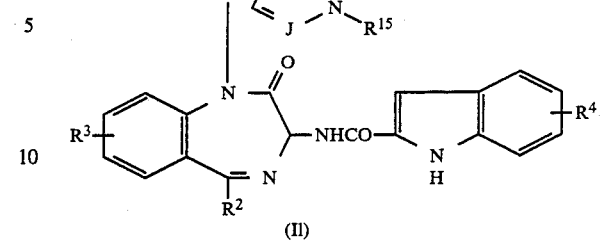

(Il)

or a salt thereof

↓ Elimination reaction of the imino protective group

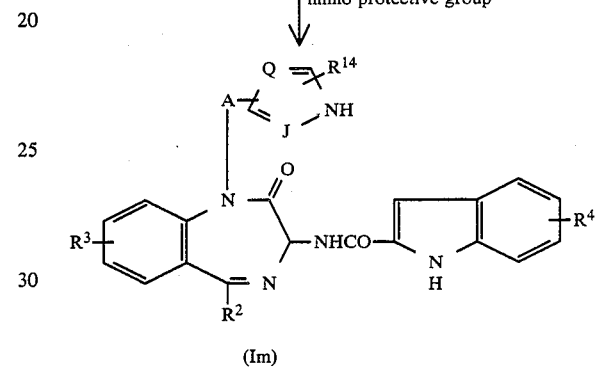

(Im)

or a salt thereof

Process 10

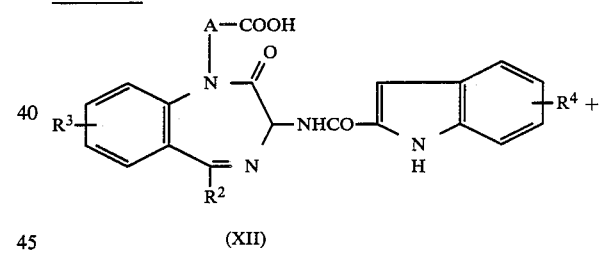

(XII)

or its reactive derivatives at the carboxy group or a salt thereof $H_2N-R^8$ ⟶

(XIII)
or its reactive derivative at the amino group or a salt thereof

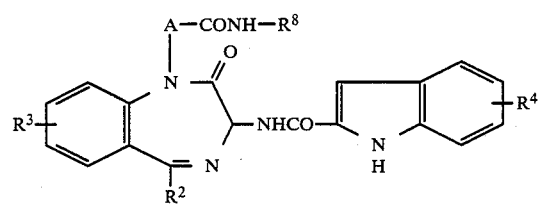

(In)

or a salt thereof

Process 11

-continued

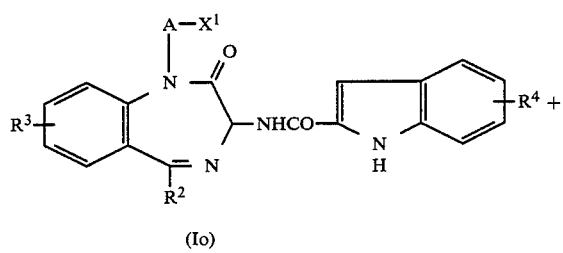

(Io)

or a salt thereof

HS—R⁶ ⟶

(XIV)
or a salt thereof

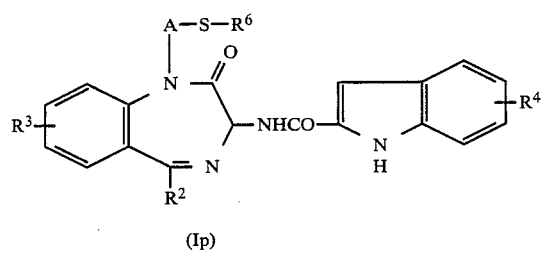

(Ip)

or a salt thereof

Process 12

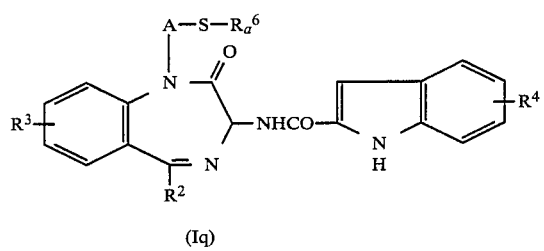

(Iq)

or a salt thereof

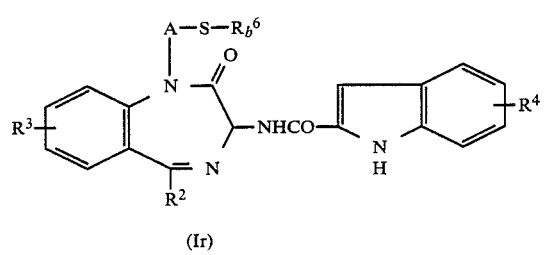

(Ir)

or a salt thereof

Process 13

-continued

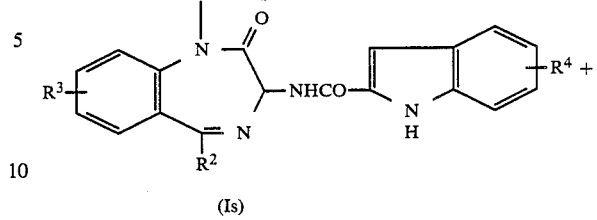

(Is)

or its reactive
derivative at the
amino group
or a salt thereof

HO—R$_a^5$ ⟶

(XV)

or its reactive
derivative at the
carboxy group or
a salt thereof

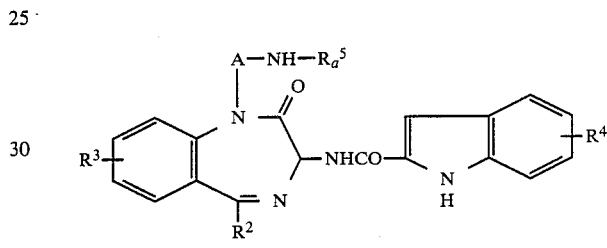

(It)

or a salt thereof

Process 14

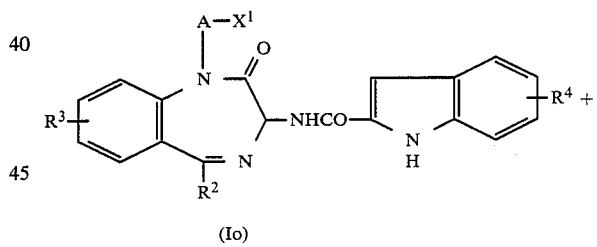

(Io)

or a salt thereof

H—R$_g^1$ ⟶

(XVI)
or a salt thereof

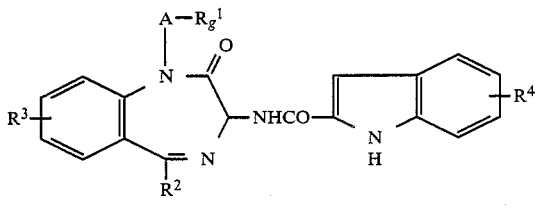

(Iu)

or a salt thereof

Process 15

-continued

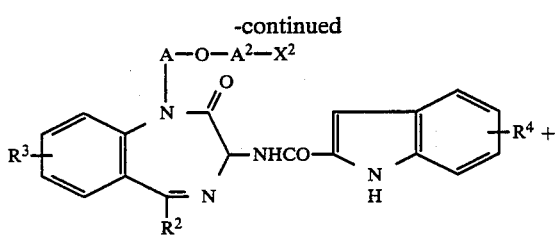

(Iv)

or a salt thereof

H—R$^{16}$ ⟶
(XVII)

or a salt thereof

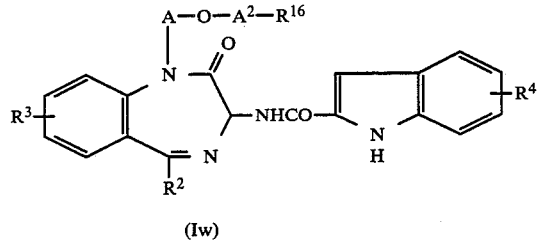

(Iw)

or a salt thereof

Process 16

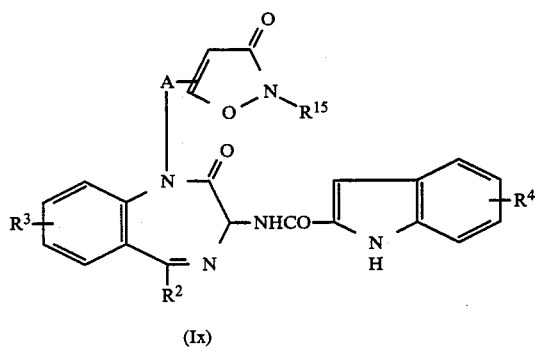

(Ix)

or a salt thereof

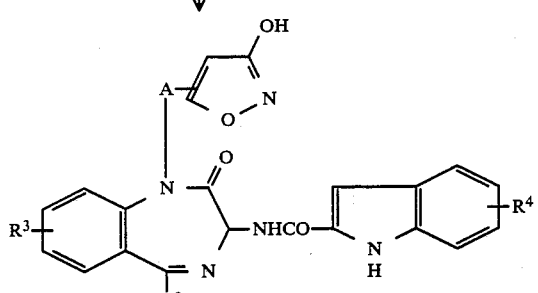

(Iy)

or a salt thereof wherein
R$^1$, R$^2$, R$^3$, R$^4$, R$^6$, R$^8$, R$^9$, R$^{10}$, R$^{11}$, R$^{12}$ and A are each as defined above, X is halogen,
R$_a^1$ is —O—R$_a^7$ in which R$_a^7$ is hydroxy protective group) or aryl having two protected hydroxy groups,
R$_b^1$ is hydroxy or aryl having two hydroxy groups,
A$^1$ is (C$_1$-C$_5$)alkylene,
R$^{13}$ is aryl,
R$_c^1$ is heterocyclic group having protected amino, phthalimido, or —O—R$_b^7$ (in which R$_b^7$ is protected amino(lower)alkyl),
R$_d^1$ is heterocyclic group having amino, amino, or —O—R$_c^7$ (in which R$_c^7$ is amino(lower)alkyl),
R$_e^1$ is

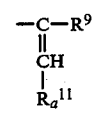

(in which R$^9$ is as defined above, R$_a^{11}$ is a protected carboxy group) or —CONH—R$_a^8$ (in which R$_a^8$ is protected carboxy(lower)alkyl),
R$_f^1$

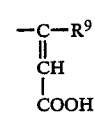

(in which R$^9$ is as defined above) or —CONH—T$_b^8$ (in which R$_b^8$ is carboxy(lower)alkyl),
R$^{14}$ is hydrogen or lower alkyl,
R$^{15}$ is an imino protective group,
J is CH or N,
Q is CH or N,
X$^1$ is halogen,
R$_a^6$ is lower alkyl substituted with protected carboxy and protected amino,
R$_b^6$ is lower alkyl substituted with carboxy and amino,
R$_a^5$ is lower alkanoyl,
R$_g^1$ is piperazinyl having lower alkyl, or —NH—R$^5$ (in which R$^5$ is as defined above),
X$^2$ is halogen,
A$^2$ is lower alkylene, and
R$^{16}$ is phthalimido or piperazinyl having lower alkyl.

The starting compound (IV) is novel and can be prepared by the following processes.

Process A

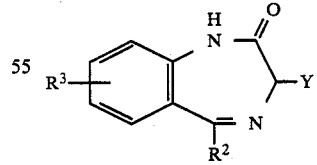

(VI)

or a salt thereof

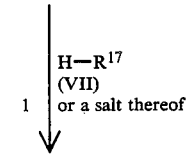

Process A

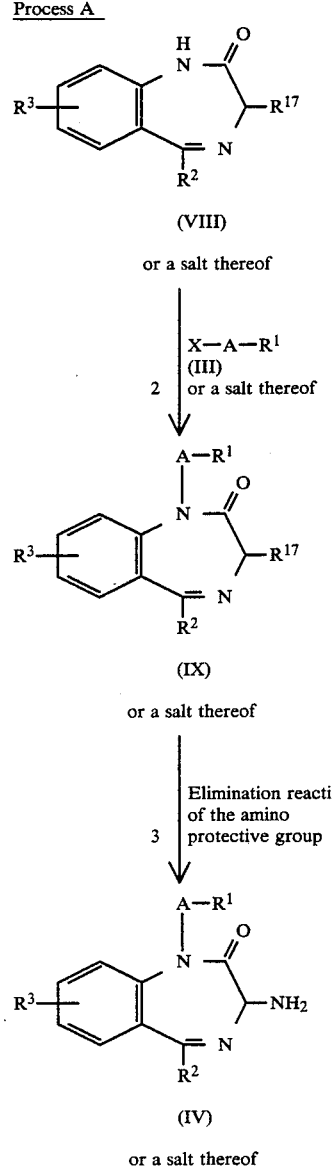

wherein
R¹, R², R³, A and X are each as defined above,
Y is an acid residue, and
R¹⁷ is a protected amino group.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "halogen" and "halogen moiety" in the term "halo(lower)alkyl" may include chlorine, bromine, fluorine and iodine.

Suitable "heterocyclic group" may include saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g. 1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

saturated 3 to 8-membered heteromonocyclic group containing 1 to 4 nitrogen atom(s), for example, pyrrolidinyl, imidazolidinyl, piperidino, piperazinyl, etc.;

unsaturated condensed heterocyclic group containing 1 to 5 nitrogen atom(s), for example, indolyl, isoindolyl, indolinyl, isoindolinyl, indolizynyl, benzimidazolyl, quinolyl, isoquinolyl, indazolyl, benzotriazolyl, tetrazolopyridyl, tetrazolopyridazinyl (e.g. tetrazolo[1,5-b]pyridazinyl, etc.), dihydrotriazolopyridazinyl, etc.;

unsaturated 3 to 8-membered heteromonocyclic group containing 1 to 2 oxygen atom(s) and 1 to 3 nitrogen atom(s), for example, oxazolyl, isoxazolyl, dihydroisoxazolyl, oxadiazolyl, (e.g., 1,2,4-oxadiazolyl, 1,3,4-oxadiazolyl, 1,2,5-oxadiazolyl, etc.) etc.;

saturated 3 to-8-membered heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.;

saturated 3 to 8-membered heteromonocyclic group containing 1 to 2 sulfur atom(s) and 1 to 3 nitrogen atom(s), for example, thiazolidinyl, etc.; unsaturated 3 to 8-membered heteromonocyclic group containing an oxygen atom, for example furyl, etc.; unsaturated 3 to 8-membered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc. and the like, and said heterocyclic group may have one or more suitable substituent(s) such as amino, protected amino, oxo, hydroxy, imino protective group (e.g., tetrahydropyranyl, trityl, etc.), lower alkyl (e.g., methyl, ethyl, propyl, isopropyl, butyl, isobutyl, sec-butyl, t-butyl, pentyl, t-pentyl, hexyl, etc.) or the like.

Suitable "aryl" and "aryl moiety" in the term "ar(-lower)alkyl" may include phenyl, naphthyl and the like.

Suitable "substituent" in "aryl which may have one or more suitable substituent(s)" for R¹ may include hydroxy, protected hydroxy, lower alkoxy (e.g., methoxy, ethoxy, propoxy, isopropoxy, butoxy, t-butoxy, pentyloxy, t-pentyloxy, hexyloxy, etc.) and the like.

Suitable "protected hydroxy" may include tetrahydropyranyloxy, acyloxy such as lower alkanoyloxy (e.g., formyloxy, acetoxy, propionyloxy, butyryloxy, isobutyryloxy, valeryloxy, isovaleryloxy, etc.), and the like.

Suitable "substituent" in "aryl which may have one or more suitable substituent(s)" for $R^2$ may include halogen (e.g., chlorine, bromine, fluorine and iodine) and the like.

Suitable "lower alkanoyl" may include formyl, acetyl, propionyl, butyryl, isobutyryl, valeryl, isovaleryl and the like.

Suitable "lower alkyl" and "lower alkyl moiety" in the terms "hydroxy(lower)alkyl", "ar(lower)alkyl", "halo(lower)alkyl", "amino(lower)alkyl", "protected amino(lower)alkyl", "piperazinyl(lower)alkyl", "carbamoyl(lower)alkyl", "carboxy(lower)alkyl" and "protected carboxy(lower)alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "protected carboxy" and "protected carboxy moiety" in the term "protected carboxy(lower)alkyl may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxy-ethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; mono(or di or tri)phenyl(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester,. etc.]; or the like.

Suitable "protected amino" and "protected amino moiety" in the term "protected amino(lower)alkyl" may include an acylamino or an amino group substituted by a conventional protective group such as ar(lower)alkyl which may have at least one suitable substituent(s), (e.g. benzyl, trityl, etc.) or the like.

Suitable acyl moiety in the terms "acylamino" and "acyloxy" may include aliphatic acyl group and acyl group containing an aromatic or heterocyclic ring.

And, suitable examples of the said acyl may be lower alkanoyl (e.g. formyl, acetyl, propionyl, butyryl, isobutyryl, valeryl, isovaleryl, oxalyl, succinyl, pivaloyl, etc.);

lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tert-butoxycarbonyl, pentyloxycarbonyl, hexyloxycarbonyl, etc.);

lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.);

aroyl (e.g. benzoyl, toluoyl, xyloyl, naphthoyl, phthaloyl, indancarbonyl, etc.);

ar(lower)alkanoyl (e.g. phenylacetyl, phenylpropionyl, etc.);

ar(lower)alkoxycarbonyl (e.g. benzyloxycarbonyl, phenethyloxycarbonyl, etc.), and the like.

The acyl moiety as stated above may have at least one suitable substituent(s) such as halogen (chlorine, bromine, fluorine and iodine), amino, lower alkoxy,carbonylamino (e.g. methoxycarbonylamino, ethoxycarbonylamino, propoxycarbonylamino, isopropoxycarbonylamino, butoxycarbonylamino, tert-butoxycarbonylamino, pentyloxycarbonylamino, hexyloxycarbonylamino, etc.) or the like.

Suitable "hydroxy protective group" may include tetrahydropyranyl, acyl group such as lower alkanoyl (e.g., formyl, acetyl, propionyl, butyryl, isobutyryl, valeryl, isovaleryl, etc.), and the like.

Suitable "lower alkenyl" may include vinyl, allyl, 1-propenyl, 1 or 2 or 3-butenyl, 1 or 2 or 3 or 4-pentenyl, 1 or 2 or 3 or 4 or 5-hexenyl and the like.

Suitable "lower alkoxy" may include methoxy, ethoxy, propoxy, isopropoxy, butoxy, t-butoxy, pentyloxy, t-pentyloxy, hexyloxy and the like, preferably one having 1 to 4 carbon atom(s).

Suitable "lower alkylene" may include straight or branched one having 1 to 6 carbon atom(s), such as methylene, ethylene, trimethylene, tetramethylene, pentamethylene, hexamethylene or the like, preferably one having 1 to 4 carbon atoms(s).

Suitable "imino protective group" may include trityl, tetrahydropyranyl and the like.

Suitable "acid residue" may include acyloxy wherein acyl moiety is as mentioned above, halogen (e.g., fluorine, chlorine, bromine and iodine) and the like.

The preferred embodiments of the object compound (I) are as follows.

Preferred embodiment of $R^1$ is halogen, thienyl, furyl, piperazinyl having lower alkyl, imidazolyl which may have trityl, imidazolyl having lower alkyl, imidazolyl having trityl and lower alkyl, pyrazolyl which may have trityl, triazolyl which may have trityl, thiazolyl having amino or protected amino (more preferably thiazolyl having amino or acylamino, most preferably thiazolyl having amino or lower alkanoylamino), isoxazolyl having hydroxy, dihydroisoxazolyl having oxo and tetrahydropyranyl, tetrazolyl, isoindolyl having two oxo groups, phenyl, phenyl having two protected hydroxy groups (more preferably phenyl having two acyloxy groups, most preferably phenyl having two lower alkanoyloxy groups), phenyl having two hydroxy groups,
phenyl having two lower alkoxy groups,
—NH—R$^5$ (in which R$^5$ is hydrogen, lower alkanoyl or hydroxy(lower)alkyl),
—S—R$^6$ [in which R$^6$ is lower alkyl, lower alkyl substituted with carboxy and amino, lower alkyl substituted with protected carboxy and protected amino (more preferably lower alkyl substituted with esterified carboxy and acylamino, most preferably lower alkyl substituted with diphenyl(lower)alkoxycarbonyl and lower alkoxycarbonylamino), or pyridyl],
—O—R$^7$ [in which R$^7$ is hydrogen, hydroxy protective group (more preferably tetrahydropyranyl or acyl, most preferably tetrahydropyranyl or lower alkanoyl), lowre alkyl, lower alkenyl, phenyl(lower)alkyl, halo(lower)alkyl, amino(lower)alkyl, protected amino(lower)alkyl (more preferably phthalimido(lower)alkyl), or
piperazinyl(lower)alkyl having lower alkyl],
—CONH—R$^8$ (in which R$^8$ is cyano, carbamoyl(lower)alkyl, carboxy(lower)alkyl, protected carboxy(lower)alkyl (more preferably esterified carboxy(lower)alkyl, most preferably lower alkoxycarbonyl(lower)alkyl), or lower alkyl substituted with carbamoyl and phenyl], or
—Z—R$^9$ [in which R$^9$ is hydrogen or lower alkyl, and Z is

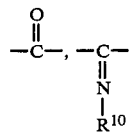

(wherein R$^{10}$ is hydroxy, lower alkoxy or amino) or

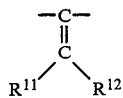

(wherein R$^{11}$ is carboxy or protected carboxy (more preferably esterified carboxy, most preferably lower alkoxycarbonyl) and
R$^{12}$ is hydrogen; or R$^{11}$ is halogen and R$^{12}$ is halogen)],
R$^2$ is phenyl or halophenyl,
R$^3$ is hydrogen,
R$^4$ is hydrogen, halogen or lower alkoxy, and
A is lower alkylene. With regard to the object compound (I), in case that the compound (I) has the group of the formula:

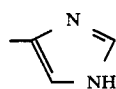

said group can also exist in the tautomeric form and such tautomeric equilibrium can be represented by the following scheme.

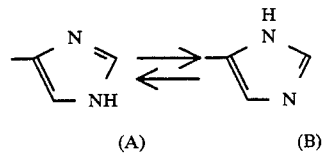

Both of the above tautomeric isomers are included within the scope of the present invention. In the present specification and claim, the compounds including the group of such tautomeric isomers are represented for the convenient sake by one expression of the group of the formula (A).

The processes for preparing the object compound (I) of the present invention are explained in detail in the following.

Process 1

The compound (I) or a salt thereof can be prepared by reacting the compound (II) or a salt thereof with the compound (III) or a salt thereof.

Suitable salts of the compounds (II) and (III) can be referred to the ones as exemplified for the compound (I).

This reaction is usually carried out in the presence of base.

Suitable base may include an inorganic base such as alkali metal hydride (e.g. sodium hydride, etc.) alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine or the like.

This reaction is usually carried out in a solvent such as alcohol (e.g., methanol, ethanol, etc.), benzene, N,N-dimethylformamide, tetrahydrofuran, diethyl ether or any other solvent which does not adversely affect the reaction.

The reaction temperature is not critical and the reaction is usually carried out at ambient temperature, under warming or under heating.

Process 2

The compound (I) or a salt thereof can be prepared by reacting the compound (IV) or its reactive derivative at the amino group or a salt thereof with the compound (V) or its reactive derivative at the carboxy group or a salt thereof.

Suitable reactive derivative at the amino group of the compound (IV) may include Schiff's base type imino or its tautomeric enamine type isomer formed by the reaction of the compound (IV) with a carbonyl compound such as aldehyde, ketone or the like; a silyl derivative formed by the reaction of the compound (IV) with a silyl compound such as N,O-bis(trimethylsilyl)acetamide, N-trimethylsilylacetamide or the like; a derivative formed by the reaction of the compound (IV) with phosphorus trichloride or phosgene, and the like.

Suitable salts of the compound (IV) and (V) can be referred to the ones as exemplified for the compound (I).

Suitable reactive derivative at the carboxy group of the compound (V) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g. methanesulfonic acid, ethanesulfonic acid, etc.), sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.), and the like. These reactive derivatives can optionally be selected from them according to the kind of the compound (V) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (V) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl 5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling to heating.

Process 3

The compound (Ib) or a salt thereof can be prepared by subjecting the compound (Ia) or a salt thereof to elimination reaction of the hydroxy protective group.

The present elimination reaction is carried out in accordance with a conventional method such as hydrolysis, reduction or the like. The hydrolysis may include a method using an acid or base and the like. These methods may be selected depending on kind of the protective groups to be eliminated.

The hydrolysis using an acid is one of the most common and preferable methods for eliminating the protective groups such as tetrahydropyranyl, benzyloxycarbonyl, substituted benzyloxycarbonyl, alkoxycarbonyl, substituted alkoxycarbonyl or the like.

Suitable acid may include, for example, formic acid, trifluoroacetic acid, benzenesulfonic acid, p-toluenesulfonic acid, hydrochloric acid, and the like. The acid suitable for the reaction can be selected according to the protective group to be eliminated and other factors.

The hydrolysis with a base is preferably applied for eliminating acyl group. Suitable base may include for example, an inorganic base such as alkali metal (e.g., sodium, potassium, etc.), alkaline earth metal (e.g., magnesium, calcium, etc.), the hydroxide or carbonate or bicarbonate thereof or the like, and an organic base such as trialkylamine (e.g., trimethylamine, triethylamine, etc.), picoline, N-methylpyrrolidine, N-methyl-morpholine or the like.

The reduction applicable for the elimination reaction of the present invention may include, for example, reduction using a metal (e.g., tin, zinc, iron, etc.) or a combination of metallic compound (e.g., chromous chloride, chromous acetate, etc.) and an organic or inorganic acid (e.g., acetic acid, propionic acid, hydrochloric acid, etc.); and reduction in the presence of a metallic catalyst for catalytic reduction. Suitable metallic catalyst for catalytic reduction may include, for example, Raney-nickel, platinum oxide, palladium carbon and other conventional catalysts. The reaction is usually carried out in a conventional solvent such as water, dioxane, tetrahydrofuran, alcohol, N,N-dimethylformamide, or any other solvent which does not adversely influence the reaction.

The reaction temperature is not critical and may be suitably selected in accordance with the kind of the protective group and the elimination method, and the present reaction is usually carried out under cooling to heating.

Process 4

The compound (Id) or a salt thereof can be prepared by subjecting the compound (Ic) or a salt thereof to oxidation reaction.

Suitable salts of the compounds (Ic) and (Id) can be referred to the ones as exemplified for the compound (I).

The present oxidation reaction can be carried out by a conventional method, for example by using an oxydizing agent such as a combination of dimethylsulfoxide with dicyclohexylcarbodiimide, a combination of chromium trioxide with pyridine, or the like.

This reaction is usually carried out in a solvent such as benzene, N,N-dimethylformamide, tetrahydrofuran, dimethylsulfoxide, chloroform, diethyl ether or any other solvent which does not adversely affect the reaction.

The reaction temperature is not critical and the reaction is usually carried out under cooling to heating.

Process 5

The compound (If) or a salt thereof can be prepared by reacting the compound (Ie) or a salt thereof with the compound (X) or a salt thereof.

Suitable salts of the compounds (Ie) and (If) can be referred to the ones as exemplified for the compound (I).

This reaction is usually carried out in a solvent such as benzene, N,N-dimethylformamide, tetrahydrofuran, chloroform, diethyl ether or any other solvent which does not adversely affect the reaction.

The reaction temperature is not critical and the reaction is usually carried out under cooling to heating.

Process 6

The compound (Ig) or a salt thereof can be prepared by reacting the compound (Ie) or a salt thereof with the compound (XI) or a salt thereof.

Suitable salts of the compound (Ig) can be referred to the ones as exemplified for the compound (I).

This reaction is usually carried out in a solvent such as benzene, N,N-dimethylformamide, tetrahydrofuran, alcohol (e.g., methanol, ethanol, etc.), chloroform, diethyl ether or any other solvent which does not adversely affect the reaction.

The reaction temperature is not critical and the reaction is usually carried out under cooling to heating.

Process 7

The compound (Ii) or a salt thereof can be prepared by subjecting the compound (Ih) or a salt thereof to elimination reaction of the amino protective group.

This reaction is carried out by substantially the same method as that of Process A ③ and therefore the reaction method and conditions can be referred to said Process A ③.

Process 8

The compound (Ik) or a salt thereof can be prepared by subjecting the compound (Ij) or a salt thereof to elimination reaction of the carboxy protective group.

This reaction is carried out by substantially the same method as that of Process 3, and therefore the reaction method and conditions can be referred to said Process 3.

Process 9

The compound (Im) or a salt thereof can be prepared by subjecting the compound (Il) or a salt thereof to elimination reaction of the imino protective group.

This reaction carried out substantially the same method as that of Process A ③ and therefore the reaction method and condition can be referred to said Process A ③.

Process 10

The compound (In) or a salt thereof can be prepared by reacting the compound (XII) or its reactive derivative at the carboxy group or a salt thereof with the compound (XIII) or its reactive derivative at the amino group or a salt thereof.

Suitable reactive derivative at the carboxy group of the compound (XII) can be referred to the ones as exemplified for the compound (V).

Suitable reactive derivative at the amino group of the compound (XIII) can be referred to the ones as exemplified for the compound (IV).

This reaction is carried out by substantially the same method as that of Process 2, and therefore the reaction method and conditions can be referred to said Process 2.

Process 11

The compound (Ip) or a salt thereof can be prepared by reacting the compound (Io) or a salt thereof with the compound (XIV) or a salt thereof.

This reaction is usually carried out in the presence of base.

Suitable base can be referred to the ones as exemplified in Process 1.

This reaction is usually carried out in a solvent such as alcohol (e.g., methanol, ethanol, etc.), benzene, N,N-dimethylformamide, tetrahydrofuran or any other solvent which does not adversely affect the reaction.

The reaction temperature is not critical and the reaction is usually carried out at ambient temperature, under warming or under heating.

Process 12

The compound (Ir) or a salt thereof can be prepared by subjecting the compound (Iq) or a salt thereof to elimination reaction of the amino protective group and the carboxy protective group.

This reaction is carried out by substantially the same method as that of Process A ③, and therefore the reaction method and conditions can be referred to said Process A ③.

Process 13

The compound (It) or a salt thereof can be prepared by reacting the compound (Is) or its reactive derivative at the amino group or a salt thereof with the compound (XV) or its reactive derivative at the carboxy group or a salt thereof.

Suitable reactive derivative at the amino group of the compound (Is) can be referred to the ones as exemplified for the compound (IV).

Suitable reactive derivative at the carboxy group of the compound (XV) can be referred to the ones as exemplified for the compound (V).

This reaction is carried out by substantially the same method as that of Process 2, and therefore the reaction method and conditions can be referred to said Process 2.

Process 14

The compound (Iu) or a salt thereof can be prepared by reacting the compound (Io) or a salt thereof with the compound (XVI) or a salt thereof.

This reaction is usually carried out in a solvent such as N,N-dimethylformamide, tetrahydrofuran, or any other solvent which does not adversely affect the reaction.

When the compound (XVI) is liquid, it can be used as a solvent.

The reaction temperature is not critical and the reaction is usually carried out at ambient temperature, under warming or under heating.

Process 15

The compound (Iw) or a salt thereof can be prepared by reacting the compound (Iv) or a salt thereof with the compound (XVII) or a salt thereof.

This reaction is carried out by substantially the same method as that of Process (I), and therefore the reaction method and conditions can be referred to said Process 1.

Process 16

The compound (Iy) or a salt thereof can be prepared by subjecting the compound (Ix) or a salt thereof to elimination reaction of the imino protective group.

This reaction is carried out by substantially the same method as that of Process 9, and therefore the reaction method and conditions can be referred to said Process 9.

The processes for preparing the starting compound (IV) are explained in the following.

Process A ①

The compound (VIII) or a salt thereof can be prepared by reacting the compound (VI) or a salt thereof with the compound (VII) or a salt thereof. The reaction method and conditions can be referred to those of Preparation 1 as mentioned below.

Process A ②

The compound (IX) or a salt thereof can be prepared by reacting the compound (VIII) or a salt thereof with the compound (III) or a salt thereof. This reaction is carried out by substantially the same method as that of Process 1, and therefore the reaction method and conditions are to be referred to said Process 1.

Process A ③

The compound (IV) or a salt thereof can be prepared by subjecting the compound (IX) or a salt thereof to elimination reaction of the amino protective group.

Suitable salts of the compound (IX) can be referred to the ones as exemplified for the compound (I).

The elimination reaction is carried out in accordance with a conventional method such as hydrolysis; reduction; Edman's method (phenyl isothiocyanate method); or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g. formyl, acetyl, etc.), cycloalkoxycarbonyl, substituted or unsubstituted aralkoxycarbonyl, aralkyl (e.g. trityl), substituted phenylthio, substituted aralkylidene, substituted alkylidene, substituted cycloalkylidene or the like. Suitable acid includes an organic or inorganic acid such as formic acid, trifluoroacetic acid, benzene-sulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated.

The elimination reaction using trifluoroacetic acid may be carried out in the presence of anisole. The hydrolysis using hydrazine is commonly applied for eliminating a phthaloyl, succinyl type aminoprotective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium on carbon and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

The reaction is usually carried out in a conventional solvent such as water, chloroform, methylene chloride, alcohol (e.g., methanol, ethanol, etc.), tetrahydrofuran or any other organic solvent which does not adversely influence the reaction.

The reaction temperature is not critical and may suitably be selected in accordance with the kind of the amino protective group and the elimination method as mentioned above, and the reaction is usually carried out under a mild condition such as under cooling or at slightly elevated temperature. Among the protective groups, the acyl group derived from α-amino acid can be eliminated by Edman's method.

The object compound (I) and pharmaceutically acceptable salts thereof are CCK antagonists and therefore useful as therapeutical agents for emesis, pancreatitis, etc. In order to show the utility of the object compound (I), CCK antagonism of the representative compound thereof is shown in the following.

CCK receptor antagonism in isolated fundic circular muscle from guinea pig stomach Test compound :

(3RS)-1,3-Dihydro-1-(2-hydroxyethyl)-3-(2- indolylcarbonylamino)-5-phenyl -2H-1,4-benzodiazepine-2-one (hereinafter referred to as test compound A)

Test method :

The strip of circular muscle suspended in 25 ml organ bath containing Kreb's bicarbonate solution (NaCl 118mM, KCl 4.8mM, $KH_2PO_4$ 1.2mM, $MgSO_4$ 1.2mM, $CaCl_2$ 2.5mM, $NaHCO_3$ 25mM, glucose 11mM and bovine serum albumin 0.1 %) maintained at 37° C. and gassed with 95% $O_2$ and 5% $CO_2$.

The strip was placed under an initial tension of 0.5 g and equilibrated for 60 minutes during which the bath volume was replaced every 15 minutes. Isometric contraction was measured using a force transducer. CCK−8 ($3.2 \times 10^{-7}$M) was added to the bathing solution and the contractile force was measured. After washing out CCK−8, test compound A ($1 \times 10^{-5}$M) was added. 5 minutes later, CCK−8 was added and the contractile force was measured. CCK antagonism was calculated by comparing the contractile force induced by CCK in the absence or presence of test compound A.
Test result
Inhibition (%) : 91

The object compound (I) or pharmaceutically acceptable salts thereof can usually be administered to mammals including human being in the form of a conventional pharmaceutical composition such as capsule, micro-capsule, tablet, granule, powder, troche, syrup, aerosol, inhalation, solution, injection, suspension, emulsion, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

A mixture of (3RS)-1,3-dihydro-3-acetoxy-5-phenyl-2H-1,4-benzodiazepine-2-one (11.75 g), potassium phthalimide (11.1 g), sodium iodide (60 g) and N,N-dimethylformamide (80 ml) was stirred for 45 minutes at 90° to 95° C. The reaction mixture was poured into a cold water (1 l). The precipitates were collected by filtration, washed with water and recrystallized from ethanol to give (3RS)-1,3-dihydro-5-phenyl-3-phthalimido-2H-1,4-benzodiazepine-2-one (8.32 g).

IR (Nujol) : 3500, 3370, 3230, 1780, 1720, 1695, 1610, 1575 cm⁻

NMR (DMSO-d6, δ) : 5.73 (1H, s), 7.30-7.70 (9H, m), 7.97 (4H, m), 11.90 (1H, br s)

Preparation 2

A mixture of (3RS)-1,3-dihydro-5-phenyl-3-phthalimido-2H-1,4-benzodiazepine-2-one (8.2 g), hydrazine hydrate (1.08 g) and tetrahydrofuran (160 ml) was stirred for 1.0 hour at room temperature and heated under reflux for 1.5 hours. After the precipitates were filtered off, the filtrate was evaporated to small volume and the equivalent volume of diisopropyl ether was added 15 thereto The precipitates were collected by filtration to give (3RS)-1,3-dihydro-3-amino-5-phenyl-2H-1,4-benzodiazepine-2-one (3.64 g).

IR (Nujol) : 3360, 3290, 2700, 1670, 1600, 1570, 1480 cm⁻

NMR (DMSO-d6, δ) : 4.30 (1H, s), 5.0 (2H, br s), 7.20-7.60 (9H, m)

Preparation 3

To a solution of (3RS)-1,3-dihydro-5-phenyl-3-phthalimido-2H-1,4-benzodiazepine-2-one (1.90 g) in N,N-dimethylformamide (30 ml) was added sodium hydride (62% suspension in mineral oil; 0.20 g) gradually with stirring under cooling in an ice-bath (<3° C.). The mixture was stirred for 10 minutes under the same conditions. To the resultant mixture was added 2-[(tetrahydropyran-2-yl)oxy]ethyl bromide (1.60 g) in one portion. The mixture was stirred at ambient temperature for one hour and at 45° C. for 4.5 hours and allowed to stand overnight. The resultant reaction mixture was poured into water and extracted with ethyl acetate twice. The extract was washed with water and dried over magnesium sulfate. Removal of the solvent gave light yellow powder, which was washed with a mixture of ethyl acetate and diethyl ether and collected by filtration to afford a mixture (1.48 g) of (3RS)-1,3-dihydro -5-phenyl-3-phthalimido-1-{2-((RS)-2-tetrahydropyranyloxy) ethyl}-2H-1,4-benzodiazepine-2-one and (3RS)-1,3-dihydro-5-phenyl-3-phthalimido-1-{2-((SR)-2tetrahydropyranyloxy)ethyl}-2H-1,4-benzodiazepine-2-one.

IR (Nujol) : 1770, 1714, 1670, 1600, 1375, 1130, 1014, 710 cm⁻¹

NMR (CDCl3, δ) : 1.3-1.9 (6H, broad), 3.4-4.7 (7H, m), 6.00.(1H, s), 7.3-8.1 (13H, m)

Preparation 4

To a solution of a mixture (0.51 g) of (3RS)-1,3-dihydro -5-phenyl-3-phthalimido-1-{2-((RS)-2-tetrahydropyranyloxy)ethyl}-2H-1,4-benzodiazepine-2-one and (3RS)-1,3-dihydro-5-phenyl-3-phthalimido-1-{2-((SR)-2tetrahydropyranyloxy)ethyl}-2H-1,4-benzodiazepine-2-one in chloroform (10 ml) was added hydrazine hydrate (55 mg) at ambient temperature under stirring. The mixture was stirred for 1.5 hours under the same conditions and heated under reflux for 1.5 hours. After cooling, the resultant precipitate was filtered off and the filtrate was evaporated to dryness. The residue was dissolved in a small amount of ethanol and diethyl ether was added thereto. White powder was filtered off again and the filtrate was evaporated to give a crude mixture (0.43 g) of (3RS)-1,3-dihydro-5-phenyl -3-amino-1-{2-((RS)-2-tetrahydropyranyloxy)ethyl}-2H-1,4-benzodiazepine-2-one and (3RS)-1,3-dihydro-5-phenyl -3-amino-1-{2-((SR)-2-tetrahydropyranyloxy)ethyl}-2H-1,4-benzodiazepine-2-one.

IR (Nujol) : 3340, 1680, 1660, 1600, 780, 760, 695 cm⁻¹

EXAMPLE 1

To a solution of (3RS)-1,3-dihydro-3-(2-indolyl-carbonylamino) -5-phenyl-2H-1,4-benzodiazepine-2-one (1.18 g) in N,N-dimethylformamide (30 ml) was added sodium hydride (62% suspension in mineral oil; 0.26 g) under stirring and cooling at 0° C. in an ice-salt bath in a nitrogen stream atmosphere. After the mixture was stirred for 40 minutes under the same conditions, 5-chloromethyltetrazole (0.39 g) was added thereto. The resultant mixture was stirred at ambient temperature for 66 hours. The reaction mixture was poured into a saturated aqueous solution of sodium bicarbonate and the aqueous solution was washed with ethyl acetate. After removal of a small amount of insoluble material by filtration, the separated aqueous layer was acidified with diluted hydrochloric acid.

The acidified aqueous mixture was extracted with ethyl acetate twice and the extract was washed with water and dried over magnesium sulfate. Removal of the solvent afforded an orange oil (1.27 g), which was chromatographed on silica gel with an eluent of a mixture of chloroform and methanol (10:1) to give the desired pure product of (3RS)-1,3-dihydro-3-(2-indolylcarbonylamino) -5-phenyl-1-(5-tetrazolylmethyl)-2H-1,4-benzodiazepine-2-one (0.5 g).

mp : 190° –195° C. (dec.)

IR (Nujol) : 3350 (sh), 3250, 1680, 1635, 1600, 740, 695 cm$^{-1}$

NMR (DMSO-d$_6$, δ) : 5.42 (2H, ABq), 5.70 (1H, d, J=8.0Hz), 6.9–8.0 (15H, m), 9.44 (1H, d, J=8 0Hz), 11.6 (1H, broad s)

Mass : m/e=447 (M=)

Example 2

To a mixture of indole-2-carboxylic acid (0.19 g), N-hydroxybenzotriazole (0.16 g) and N,N'-dicyclohexylcarbodiimide (0.24 g) in chloroform (10 ml) was added amino-1-{2-((RS)-2-tetrahydropyranyloxy)ethyl}-2H-1,4- benzodiazepine-2-one and (3RS)-1,3-dihydro-5-phenyl-3-amino-1-{2-((SR) -2-tetrahydropyranyloxy)ethyl}-2H-1,4-benzodiazepine-2-one at ambient temperature under stirring. The mixture was stirred for 2 hours under the same conditions. The resultant precipitate was filtered off. The combined filtrate and washings were evaporated under reduced pressure and the residual oil (1.20 g) was subjected to column chromatography on silica gel with an eluent of a mixture of chloroform and ethyl acetate (10:1) to give a mixture (white powder, 0.45 g) of (3RS)-1,3-dihydro-3-(2-indolylcarbonylamino) -5-phenyl-1-{2-((RS)-2-tetrahydropyranyloxy)ethyl}-2H-1,4-benzodiazepine-2-one and (3RS)-1,3-dihydro-3-(2-indolylcarbonylamino)-5-phenyl-1-{2-((SR) -2-tetrahydropyranyloxy)ethyl}-2H-1,4-benzodiazepine-2-one.

IR (Nujol) : 3340, 3280, 1680, 1630, 1610 (sh), 750, 700 cm$^{-1}$

NMR (CDCl$_3$, δ) : 1.0–2.0 (6H, m), 3.1–4.7 (7H, m), 5.82 (1H, d, J=8Hz), 7.0–7.9 (14H, m), 8.13 (1H, d, J=8Hz), 9.62 (1H, broad)

Example 3

To a suspension of a mixture (0.42g)of (3RS)-1,3-dihydro -3-(2-indolylcarbonylamino)-5-phenyl-1-{2-((RS)-2-tetrahydropyranyloxy)ethyl}-2H-1,4-benzodiazepine-2-one and (3RS)-1,3-dihydro-3-(2-indolylcarbonylamino)-5-phenyl -1-{2-((SR)-2-tetrahydropyranyloxy)ethyl}-2H-1,4-benzodiazepine -2-one in acetone (10 ml) was added 6N-hydrochloric acid (0.4 ml) under stirring at ambient temperature. After the yellow clear solution was stirred for 45 minutes, the additional 6N-hydrochloric acid (0.4 ml) and water (1 ml) were added thereto. The mixture was stirred for 0.5 hour at ambient temperature. Neutralization with an aqueous solution of sodium bicarbonate and removal of acetone gave yellow precipitates, which were collected by filtration, washed with water and dried. The crude product was purified by column chromatography on silica gel with an eluent of a mixture of chloroform and ethyl acetate (5:1) to afford pure (3RS)-1,3-dihydro-1-(2-hydroxyethyl)-3-(2-indolylcarbonylamino) -5-phenyl-2H-1,4-benzodiazepine-2-one (0.28 g) as an amorphous. This was triturated in diethyl ether to give light yellow powder.

mp : 170° –175° C. (dec.)

IR (Nujol) : 3400 (sh), 3260, 1675 (sh), 1630, 1595, 740, 690 cm$^{-1}$

NMR (CDCl$_3$, δ) : 2.32 (1H, broad), 3.65–4.4 (4H, m), 5.74 (1H, d, J=8Hz), 7.05–7.7 (14H, m), 8.02 (1H, d, J=8Hz), 9.45 (1H, broad s) MASS : m/e=438 (M+)

Preparation 5

(1) To a solution of a mixture (1.0 g) of (3R)-1,3-dihydro-5-phenyl-3-[((2S) -2-tert-butoxycarbonylamino-3phenylpropanoyl)amino]-2H-1,4-benzodiazepine-2-one and (3S)-1,3-dihydro-5-phenyl-3-[((2S)-2-tert-butoxycarbonyl-amino -3-phenylpropanoyl)amino]-2H-1,4-benzodiazepine-2-one in N,N-dimethylformamide (5 ml) was added sodium hydride (77.4 mg, 62% suspension in mineral oil) under stirring with cooling in an ice-bath (ca. 3° C.). The mixture was stirred for 40 minutes under the same condition. To the resultant mixture was added 2-acetoxyethyl bromide (0.37 g) at once under stirring and cooling. The mixture was stirred for 1.5 hours under ice-cooling and for 2 hours at ambient temperature. The reaction mixture was poured into water and extracted with ethyl acetate twice. The extracts were combined, washed with brine and dried over magnesium sulfate. Removal of the solvent by evaporation gave an oil (1.29 g), which was subjected to column chromatography on silica gel with an eluent of a mixture of chloroform and ethyl acetate (10:1). The fractions containing the desired compound were combined and evaporated to afford a colorless oily mixture (0.84 g) of (3R)-1-(2-acetoxyethyl)-1,3-dihydro-5-phenyl-3-[((2S)-2-tert-butoxycarbonylamino -3-phenylpropanoyl)amino]-2H-1,4-benzodiazepine-2-one and (3S)-1-(2-acetoxyethyl)-1,3-dihydro-5-phenyl-3-[((2S) -2-tert-butoxycarbonylamino-3phenylpropanoyl)amino]-2H-1,4-benzodiazepine-2-one.

IR (liquid) : 3400 (shoulder), 3300, 1730, 1700 (shoulder), 1690, 1660, 1600, 745, 695 cm$^{-1}$ NMR (CDCl$_3$, δ) : 1.40 (9H, s), 1.62 (3H, s), 3.0–3.3 (2H, m), 3.9–4.2 (3H, m), 4.4–4.8 (2H, m), 5.06 (1H, broad d), 5.51 & 5.53 (1H, d & d), 7.2–7.85 (14H, m)

The following compound was obtained according to a similar manner to that of Preparation 5(1).

(2) Mixture of (3R)-1-(2-acetoxyethyl)-1,3-dihydro-5-(2-fluorophenyl)-3-[((2S) -2-tert-butoxycarbonylamino-3-phenylpropanoyl)amino]-2H-1,4-benzodiazepine-2-one and (3S)-1-(2-acetoxyethyl)-1,3-dihydro-5-(2-fluorophenyl)-3-[((2S)-2-tert-butoxycarbonylamino-3phenylpropanoyl)amino]-2H-1,4-benzodiazepine-2-one IR (liquid) 3400 (shoulder), 3320, 1730, 1700 (shoulder), 1690, 1662, 1485, 1440, 1380, 1365, 1230, 1161, 1048, 750, 695 cm$^{-1}$ NMR (CDCl$_3$, δ) : 1.40 (9H, s), 1.79 (3H, s), 3.0–3.3 (2H, m), 3.4–4.8 (5H, m), 5.07 (1H, broad d, J=7.4Hz), 5.53, 5.55 (1H, dd, J=8Hz), 6.95–7.9 (14H, m)

Preparation 6

To a solution of a mixture (0.7 g) of (3R)-1-(2-acetoxyethyl) -1,3-dihydro-5-phenyl-3-[((2S)-2-tert-butoxycarbonylamino-3-phenylpropanoyl)amino]-2H-1,4-benzodiazepine-2-one and (3S)-1-(2-acetoxyethyl)-1,3-dihydro-5-phenyl-3-[((2S)-2-tert-butoxycarbonylamino-3-phenylpropanoyl)amino]-2H-1,4-benzodiazepine-2-one in ethyl acetate (20 ml) was introduced hydrogen chloride gas under cooling in an ice-bath with stirring. After the solution was saturated with hydrogen chloride, the mixture was stirred for 30 minutes under the same temperature and for 1 hour at ambient temperature. After removal of the hydrogen chloride by bubbling dried nitrogen gas, the mixture was evaporated under reduced pressure. To the residue was added water and the mixture was neutralized with a saturated aqueous solution of sodium bicarbonate. The mixture was extracted with ethyl acetate twice and the extract was washed with water and dried over magnesium sulfate. Removal of the solvent afforded a mixture (0.57 g) of (3R)-1-(2-acetoxyethyl)-3-[((2S)-2-amino-3-phenylpropanoyl)amino]-1,3-dihydro-5-phenyl-2H-1,4-benzodiazepine-2-one and (3S)-1-(2-acetoxyethyl)-3-[((2S)-2-amino-3phenylpropanoyl)amino]-1,3-dihydro-5-phenyl-2H-1,4-benzodiazepine-2-one.

Preparation 7

A mixture (12.2 g) of (3R)-1-(2-acetoxyethyl)-3[((2S)-2-amino-3-phenylpropanoyl)amino]-1,3-dihydro-5-phenyl-2H-1,4-benzodiazepine-2-one (3R-isomer) and (3S)-1-(2-acetoxyethyl)-3-[((2S) -2-amino-3-phenylpropanoyl)amino]-1,3-dihydro-5-phenyl-2H-1,4-benzodiazepine-2-one (3S-isomer) was subjected to a column chromatography on silica gel (230-400 mesh) with an eluent of a mixture of chloroform and methanol (20:1). The fractions containing the object compound were combined and evaporated to dryness to give pure 3S-isomer (3.32 g) as an oil. From the other fractions, an oily mixture (8.50 g) of 3S-isomer and 3R-isomer was obtained. The oily mixture was re-chromatographed on silica gel (230-400 mesh) with an eluent of a mixture of chloroform and methanol (15:1) to give an oily pure 3S-isomer (1.30 g) and an oily pure 3R-isomer (4.01 g).

NMR (CDCl$_3$+D$_2$O, δ) 270 MHz :

3S-isomer 1.648 (3H, s), 2.817 (1H, dd, J=14.0Hz, 10.8Hz), 3.336 (1H, dd, J=14Hz, 6.5Hz), 3.704 (1H, dd, J=10.8Hz, 6.5Hz), 3.927 (1H, dt, J=15.1Hz, 6.5Hz), 4.07-4.20 (2H, m), 4.660 (1H, octet, J=13.6Hz, 7.6Hz, 7.6Hz), 5.578 (1H, s), 7.19-7.64 (14H, m)

3R-isomer 1.642 (3H, s), 2.696 (1H, dd, J=14.0Hz, 10.8Hz), 3.349 (1H, dd, J=14.0Hz, 6.5Hz), 3.729 (1H, dd, J=10.8Hz, 6.5Hz), 3.927 (1H, dt, J=15.1Hz, 6.5Hz), 4 09-4.17 (2H, m), 4.690 (1H, octet, J=13.6Hz, 7.6Hz, 7.6Hz), 5,571 (1H, s), 7.21-7.63 (14H, m)

Preparation 8

The following compounds were obtained according to similar manners to those of Preparations 6 and 7.

(3S)-1-(2-Acetoxyethyl)-3-[((2S)-2-amino-3phenylpropanoyl)amino]-1,3-dihydro-5-(2-fluorophenyl)-H-1,4-benzodiazepine-2-one mp : 168° -170° C.

IR (Nujol) : 3410, 3360, 3325 (sh), 1742, 1680 (sh), 1667, 1610 (sh), 1600, 1480, 1448, 1240, 1108, 1045, 810, 781, 730, 699 cm$^{-1}$ NMR (CDCl$_3$, δ) : 1.81 (3H, s), 1.85 (2H, s), 2.84 (1H, dd, J=10.5Hz, 13.5Hz), 3.33 (1H, dd, J=13.5Hz, 4Hz), 3.69-4.25 (4H, m), 4.5-4.8 (1H, m), 5.60 (1H, d, J=8Hz), 6.95-7.9 (13H, m), 9.01 (1H, d, J=9Hz)

(3R)-1-(2-Acetoxyethyl)-3-[((2S)-2-amino-3phenylpropanoyl)amino]-1,3-dihydro-5-(2-fluorophenyl)-H-1,4-benzodiazepine-2-one IR (Film) : 3400 (sh), 3360, 1738, 1685 (sh), 1668, 1605, 1510 (sh), 1495, 1450, 1380, 1328, 1240, 1220, 1108, 1045, 820, 750, 700 cm$^{-1}$ NMR (CDCl$_3$, δ) : 1.80 (3H, s), 1.87 (2H, s), 2.73 (1H, dd, J=13.5Hz, 10.5Hz), 3.39 (1H, dd, J=13.5Hz, 4Hz), 3.7-4.25 (4H, m), 4 5-4.8 (1H, m), 5.61 (1H, d, J=8Hz), 6.95-7.9 (13H, m), 9.04 (1H, d, J=8Hz)

Preparation 9

(1) A solution of (3S)-1-(2-acetoxyethyl)-3-[((2S)-2-amino-3-phenylpropanoyl)amino]-1,3-dihydro-5-phenyl-2H-1,4-benzodiazepine-2-one (4.65 g) and phenyl isothiocyanate (1.43 g) in methylene chloride (100 ml) was heated on steam bath under stirring After removal of the solvent, methylene chloride (100 ml) was added to the residue. The procedure described above was repeated three times. Then the methylene chloride was removed completely under reduced pressure to give an oily intermediate (thiourea derivative). To the oil was added trifluoroacetic acid (80 ml) and the mixture was warmed on water bath set at 52° C under stirring for 20 minutes. Removal of the solvent under reduced pressure and the residue was treated with methylene chloride and diethyl ether twice respectively to give an viscous red oil, which was subjected to column chromatography on silica gel with an eluent of a mixture of chloroform and methanol (15:1). The fractions containing the desired compound were combined and evaporated to afford an orange oil (2.24 g). The oil was dissolved in ethyl acetate and washed with a small amount of an aqueous solution of sodium bicarbonate. The organic layer was separated and dried over magnesium sulfate. Removal of the solvent gave (3S)-1-(2-acetoxyethyl) -3-amino-1,3-dihydro-5-phenyl-2H-1,4-benzodiazepine-2-one (1.35 g).

IR (Film) : 3370, 3300, 1725, 1665, 1600 cm$^{-1}$

NMR (CDCl$_3$, δ) : 1.66 (3H, s), 2.90 (2H, br s), 3.8-4.8 (5H, m), 7.1-7.8 (9H, m)

$[α]_D^{26.8}$ : -111.73° (0.00260 g/ml, CHCl$_3$)

The following compounds were obtained according to a similar manner to that of Preparation 9(1).

(2) (3R)-1-(2-Acetoxyethyl)-3-amino-1,3-dihydro-5-phenyl-2H-1,4-benzodiazepine -2-one IR (Film) : 3370, 3300, 1725, 1665, 1600 cm$^{-1}$ NMR (CDCl$_3$, δ) : 1.66 (3H, s), 2.89 (2H, br s), 3.8-4.8 (5H, m), 7.1-7.8 (9H, m)

$[α]_D^{26.8}$ : 123.63° (0.00312 g/ml, CHCl$_3$)

(3) (3S)-1-(2-Acetoxyethyl)-3-amino-1,3-dihydro-5-(2-fluorophenyl) -2H-1,4-benzodiazepine-2-one IR (Film) : 3450 (sh), 3380, 3325 (sh), 1738, 1680, 1660 (sh), 1605, 1580, 1490, 1455, 1375, 1332, 1230, 1110, 1050, 820, 760, 745 cm$^{-1}$ NMR (CDCl$_3$, δ) : 1.81 (3H, s), 3.8-4.8 (6H, m), 6 95-7.9 (9H, m)

$[α]_D^{25}$ : -57.68° (3.10 mg/ml, CH$_2$Cl$_2$)

(4) (3R)-1-(2-Acetoxyethyl)-3-amino-1,3-dihydro-5-(2-fluorophenyl) -2H-1,4-benzodiazepine-2-one IR (Film) : 3450 (sh), 3350, 3325 (sh), 1736, 1690 (sh), 1673, 1650 (sh), 1600, 1580, 1482, 1450, 1370, 1328, 1222, 1105, 1000, 815, 750 cm$^{-1}$ NMR (CDCl$_3$, δ) : 1.80 (3H, s), 3.8-4.8 (6H, m), 6.95-7.9 (9H, m)

$[α]_D^{25}$ : 50.52° (3.18 mg/ml, CH$_2$Cl$_2$)

EXAMPLE 4

(1) To a solution of (3S)-1-(2-acetoxyethyl)-3-amino-1,3-dihydro-5-phenyl -2H-1,4-benzodiazepine-2-one (1.35 g) in N,N-dimethylformamide (25 ml) were added indole-2-carboxylic acid (0.64 g), N-hydroxybenzotriazole (0.54 g) and N,N'-dicyclohexylcarbodiimide (0.83 g) under stirring at ambient temperature. The mixture was stirred for 2 hours at the same temperature and allowed to stand overnight. The resultant precipitates were filtered off and the filtrate and the washings were combined. The solvent (N,N-dimethylformamide) was evaporated under reduced pressure To the residue was added water and the mixture was extracted with ethyl acetate. The extract was washed with brine twice and dried over magnesium sulfate Removal of the solvent afforded an oil (3.05 g), which was subjected to column chromatography on silica gel with an eluent of a mixture of chloroform and methanol (15:1). The fractions containing the desired product were combined and evaporated under reduced pressure to give (3S)-1-(2-acetoxyethyl)-3-(2-indolylcarbonylamino) -1,3-dihydro5-phenyl-2H-1,4-benzodiazepine-2-one (1.90 g).

IR (Nujol) : 3325, 3260, 1735, 1680, 1630, 1600, 1230, 745, 697 cm$^{-1}$

NMR (CDCl$_3$, δ) : 1.65 (3H, s), 3.8–4.3 (3H, m), 4.55–4.9 (1H, m), 5.84 (1H, d, J=8.25Hz), 7.0–7.8 (14H, m), 8.14 (1H, d, J=8.25Hz), 9.98 (1H, br s)

MASS : m/e=481(M$^-$)

$[α]_D^{26.8}$ : -51.27° (0.00340 g/ml, CHCl$_3$)

The following compounds were obtained according to a similar manner to that of Example 4(1).

(2) (3R)-1-(2-Acetoxyethyl)-3-(2-indolylcarbonylamino)-1,3-dihydro-5-phenyl -2H-1,4-benzodiazepine-2-one.

IR (Nujol) : 3325, 3260, 1735, 1680, 1630, 1600, 1230, 745, 697 cm$^{-1}$

NMR (CDCl$_3$, δ) : 1.65 (3H, s), 3.8–4.3 (3H, m), 4.55–4.9 (1H, m), 5.84 (1H, d, J=8.25Hz) 7.0–7.8 (14H, m), 8.14 (1H, d, J=8.25Hz), 10.06 (1H, br s)

MASS : m/e=481 (M$^-$)

$[α]_D^{26.8}$: 58.90° (0.00300 g/ml, CHCl$_3$)

(3) (3S)-1-(2-Acetoxyethyl)-3-(2-indolylcarbonylamino) -1,3-dihydro-5-(2-fluorophenyl)-2H-1,4-benzodiazepine-2-one mp : 183° –187° C. (dec.)

IR (Nujol) : 3350 (sh), 3275, 1733, 1687, 1640, 1610 (sh), 1539, 1455, 1380, 1260, 1235, 821, 775, 750 cm$^{-1}$ NMR (CDCl$_3$, δ) : 1.80 (3H, s), 3.8–4.25 (3H, m), 4.45–4.85 (1H, m), 5.84 (1H, d, J=8Hz), 6.9–7.9 (13H, m), 8.15 (1H, d, J=8Hz), 10.11 (H, broad s)

MASS : m/e=498 (M$^+$)

(4) (3R)-1-[2-Acetoxyethyl)-3-(2-indolylcarbonylamino) -1,3-dihydro-5-(2-fluorophenyl)-2H-1,4-benzodiazepine-2-one mp : 185° –189° C. (dec.)

IR (Nujol) : 3325 (sh), 3260, 1726, 1682, 1635, 1610 (sh), 1535, 1448, 1372, 1255, 1226, 820, 770, 745 cm$^{-1}$ NMR (CDCl$_3$, δ) : 1.81 (3H, s), 3.8–4.3 (3H, m), 4.55–4.85 (1H, m), 5.84 (1H, d, J=8Hz), 6.9–7.85 (13H, m), 8.14 (1H, d, J=8Hz), 10.00 (1H, broad s)

MASS : m/e=498 (M$^+$)

EXAMPLE 5

(1) A mixture of (3S)-1-(2-acetoxyethyl)-3-(2-indolylcarbonylamino) -1,3-dihydro-5-phenyl-2H-1,4-benzodiazepine-2-one (1.80 g) and potassium carbonate (0.30 g) in 85% aqueous ethanol (30 ml) was heated at 65° to 70° C. for 1 hour under stirring. After cooling, ethanol was removed under reduced pressure, and to the residue was added water. The aqueous mixture was acidified with dilute hydrochloric acid and extracted with ethyl acetate. The extract was washed with brine and dried over magnesium sulfate. Removal of the solvent afforded a light yellow amorphous powder, which was chromatographed on silica gel with an eluent of a mixture of chloroform and ethyl acetate (3:1). The fractions containing the desired product were combined and evaporated to give (3S)-1-(2-hydroxyethyl)-3-(2-indolylcarbonylamino) -1,3-dihydro-5-phenyl-2H-1,4-benzodiazepine-2-one (1.47 g) as a colorless amorphous powder.

IR (Nujol) : 3400 (shoulder), 3260, 1680, 1635, 15 1600, 745, 695 cm$^{-1}$

NMR (CDCl$_3$, δ) : 2.7 (1H, br s), 3.65–4.3 (4H, m), 5.79 (1H, d, J=8Hz), 7.0–7.9 (14H, m), 8.17 (1H, d, J=8Hz), 10.15 (1H, br s).

MASS : m/e=438 (M$^+$)

$[α]_D^{26.8}$ : 59.04° (0.00352 g/ml, CHCl$_3$)

The following compounds were obtained according to a similar manner to that of Example 5(1).

(2) (3R)-1-(2-Hydroxyethyl)-3-(2-indolylcarbonylamino) -1,3-dihydro-5-phenyl-2H-1,4-benzodiazepine-2-one.

IR (Nujol) : 3400 (shoulder), 3260, 1680, 1635, 1600, 740, 695 cm.$^{-1}$

NMR (CDCl$_3$ δ) : 2.83 (1H, br s), 3.55–4.3 (4H, m), 5.78 (1H, d, J=8Hz), 6.9–7.8 (14H, m), 8.18 (1H, d, J=8Hz), 10.28 (1H, br s)

MASS : m/e=438 (M$^+$)

$[α]_D^{26.8}$: 69.16° (0.00360 g/ml, CHCl$_3$)

(3) (3S)-1-(2-Hydroxyethyl)-3-(2-indolylcarbonylamino)-1,3-dihydro-5-(2-fluorophenyl) -2H-1,4-benzodiazepine-2-one mp : 190° –195° C. (dec.)

IR (Nujol) : 3400 (sh), 3270, 1680 (sh), 1640, 1610 (sh), 1535, 1485, 1450, 1379, 1330, 1220, 818, 770 (sh), 748 cm$^{-1}$ NMR (CDCl$_3$, δ) : 2.17 (1H, s), 3.7–4.55 (4H, m), 5.79 (1H, d, J=8Hz), 6.9-7.85 (13H, m), 8.12 (1H, d, J=8Hz), 9.81 (1H, broad s)

MASS : m/e=456 (M$^+$)

$[α]_D^{25}$ : 1.20° (3.32 mg/ml, CHCl$_3$)

(4) (3R)-1-(2-Hydroxyethyl)-3-(2-indolyl-carbonylamino) -1,3-dihydro-5-(2-fluorophenyl)-2H-1,4-benzodiazepine-2-one mp : 190° –195° C. (dec.)

IR (Nujol) : 3400 (sh), .3270, 1680 (sh), 1639, 1610 (sh), 1533, 1484, 1450, 1378, 1330, 1220, 818, 770 (sh), 745 cm$^{-1}$ NMR (CDCl$_3$, δ) : 1.91 (1H, s), 3.7-4.55 (4H, m), 5.79 (1H, d, J=8Hz), 6.9-7.85 (13H, m), 8.08 (1H, d, J=8Hz), 9.61 (1H, broad s)

MASS : m/e=456 (M$^+$)

$[α]_d^{25}$ : 0.99° (3.26 mg/ml, CHCl$_3$)

EXAMPLE 6

(1) To a solution of (3RS)-1,3-dihydro-3-(2-indolylcarbonylamino) -5-phenyl-2H-1,4-benzodiazepine-2one (394 mg) in N,N-dimethylformamide (4 ml) was added sodium hydride (62% suspension in mineral oil, 44 mg) under stirring at 0° C. in an ice-bath. The mixture was stirred for 1.0 hour at 0° to −5° C. 2-Methoxyethyl chloride (142 mg) was added thereto. The mixture was stirred for 6.0 hours at 60° to 70° C. and cooled. To the cooled reaction mixture were added acetic acid (0.5 ml), ethyl acetate (40 ml) and water (40 ml) under stirring. The organic layer was separated, washed with an aqueous solution of sodium bicarbonate and water, dried over magnesium sulfate and evaporated. The residue was chromatographed on silica gel with chloroform as an eluent to give the pure product of (3RS)-1,3-dihydro-3(2-indolylcarbonylamino) -5-phenyl-1-(2-methoxyethyl)-2H-1,4-benzodiazepine-2-one (110 mg).

mp : 180°-185° C. (dec.)

IR (Nujol) : 3440, 3275, 1685, 1630, 1600, 1540, 1490 cm$^{-1}$

NMR (CDCl$_3$, δ) : 3.13 (3H, s), 3.45–3.65 (2H, m), 3.80–4.50 (2H, m), 5.80 (1H, d, J=8Hz), 7.0–7.80 (14H, m), 8.15 (1H, d, J=8Hz), 9 75 (1H, s)

The following compound was obtained according to a similar manner to that of Example 6(1).

(2) (3RS)-1-Acetylmethyl-1,3-dihydro-3-(2-indolylcarbonylamino) -5-phenyl-2H-1,4-benzodiazepine-2-one IR (Nujol) : 3325, 3250, 1720, 1680, 1630, 1530, 1448, 1375, 740, 695 cm$^{-1}$ NMR (DMSO-d$_6$, δ) : 2.16 (3H, s), 4.71 (2H, s), 5.90 (1H, d, J=7.5Hz), 7.0–7.75 (14H, m), 8.09 (1H, d, J=7.5Hz), 10.01 (1H, broad s)

MASS : m/e=450 (M$^+$)

EXAMPLE 7

(3RS)-1,3-Dihydro-1-(2-hydroxyethyl)-3-(2-indolylcarbonylamino) -5-phenyl-2H-1,4-benzodiazepine-2-one (0.30 g) was dissolved in a mixture of anhydrous dimethylsulfoxide (1 ml) and benzene (1 ml) containing pyridine (0.056 ml) and trifluoroacetic acid (0.028 ml). After addition of dicyclohexylcarbodiimide (0.42 g), the mixture was stirred overnight at room temperature. Water was added thereto and the insoluble dicyclohexylurea was removed by filtration. The filtrate was extracted with ethyl acetate twice and the organic layer was washed with water, aqueous sodium bicarbonate and water respectively. The extract was dried over magnesium sulfate and evaporated to give an amorphous oil (0.53 g), which was subjected to column chromatography on silica gel with a mixture of chloroform and ethyl acetate (5:1) as an eluent. The fractions containing the objective materials were combined and evaporated to afford white powder, which was purified by washing with diisopropyl ether to give pure (3RS)-1,3-dihydro-1-formylmethyl-3-(2-indolylcarbonylamino)-5-phenyl -2H-1,4-benzodiazepine-2-one (0.20 g).

mp : 168° C. (dec.)

IR (Nujol) : 3400 (shoulder), 3270, 1725, 1680, 1635, 1600, 1445, 1375, 745, 695 cm$^{-1}$ NMR (CDCl$_3$, δ) : 4.68 (2H, s), 5.90 (1H, d, J=7.5Hz), 7.0–7.75 (14H, m), 8.07 (1H, d, J=7.5Hz), 9.66 (1H, s), 10.05 (1H, broad s)

MASS : m/e=436 (M$^+$)

EXAMPLE 8

To a solution of (3RS)-1,3-dihydro-1-formylmethyl-3-(2-indolylcarbonylamino) -5-phenyl-2H-1,4-benzodiazepine-2-one (0.44 g) in chloroform (10 ml) was added methoxycarbonylmethylenetriphenylphosphorane (0.37 g). The mixture was stirred at room temperature for 2 hours. The reaction mixture was concentrated to give a residual oil, which was subjected to column chromatography on silica gel with a mixture of chloroform and ethyl acetate (10:1) as an eluent.

(3RS)-1,3-dihydro-1-[(Z)-3-methoxycarbonyl-2-propenyl) -3-(2-indolylcarbonylamino)-5-phenyl-2H-1,4-benzodiazepine-2-one (64.6 mg) was obtained from the former fractions.

IR (Nujol) : 3340, 3250, 1718, 1700, 1665, 1637, 1598, 1536, 1450, 1375, 805, 740, 690 cm$^{-1}$ NMR (CDCl$_3$, δ) : 3.74 (3H, s), 5.24 (2H, dd, J=6Hz, 1.5Hz), 5.86 (1H, d, J=8Hz), 5.90 (1H, dt, J=12.7Hz, 1.5Hz), 6.21 (1H, dt, J=12.7Hz, 6Hz), 7.1–7.8 (14H, m), 8.13 (1H, d, J=8Hz), 9.98 (1H, broad s)

(3RS)-1,3-dihydro-1-[(E)-3-methoxycarbonyl-2-propenyl) -3-(2-indolylcarbonylamino)-5-phenyl-2H-1,4-benzodiazepine-2-one (291.1 mg) was obtained from the later fractions.

IR (Nujol) : 3340, 3270, 1711, 1685, 1635, 1600, 1535, 1450, 1375, 830, 772, 740, 700 cm$^{-1}$ NMR (CDCl$_3$, δ) : 3.64 (3H, s), 4.7–4.82 (2H, m), 5.87 (1H, d, J=7.5Hz), 5.88 (1H, dt, J=16.5Hz, 1.5Hz), 6.94 (1H, dt, J=16.5Hz, 4.5Hz), 7.1–7.8 (14H, m), 8.11 (1H, d, J=7.5Hz), 9.92 (1H, broad s)

EXAMPLE 9

A mixture of (3RS)-1-acetylmethyl-1,3-dihydro-3-(2-indolylcarbonylamino) -5-phenyl-2H-1,4-benzodiazepine-2-one (0.30 g) and hydrazine hydrate (36.0 mg) in tetrahydrofuran (5 ml) was refluxed for 15 hours and concentrated to give an amorphous materials (0.30 g).

This material (0.30 g) was chromatographed on silica gel with a mixture of chloroform and methanol (30:1). After the solvent was removed from the fractions containing the objective compound, the residue was pulverized in diisopropyl ether to give (3RS)-1-(2-hydrazonopropyl) -1,3-dihydro-3-(2-indolylcarbonylamino)-5-phenyl-2H-1,4-benzodiazepine-2-one (white powder, 178 mg).

mp : 187° C. (dec.)

IR (Nujol) : 3400 (shoulder), 3250, 1680, 1630, 1600, 1528, 1450, 1374, 800, 760, 740, 690 cm$^{-1}$ NMR (CDCl$_3$, δ) : 1.53 (3H, s), 4.75 (2H, ABq), 5 5.90 (2H, broad s), 5.87 (1H, d, J=7.5Hz), 7.0–7.75 (14H, m), 8.16 (1H, d, J=7.5Hz), 9.67 (1H, broad s)

MASS : m/e=464 (M$^+$)

EXAMPLE 10

A mixture of (3RS)-1-acetylmethyl-1,3-dihydro-3-(2-indolylcarbonylamino) -5-phenyl-2H-1,4-benzodiazepine-2-one (0.42 g), hydroxylamine hydrochloride (62.5 mg) in ethanol (20 ml) was stirred at room temperature for 40 hours. The mixture was evaporated to dryness and the residue was subjected to column chromatography on silica gel with an eluent of a mixture of chloroform and methanol (40:1). The fractions containing the objective product were combined and evaporated to give a pale green oil, which was pulverized in diisopropyl ether to afford (3RS)-1-(2-hydroxyiminopropyl)-1,3-dihydro-3-(2-indolylcarbonylamino) -5-phenyl-2H-1,4-benzodiazepine-2-one (177 mg).

mp : 187° C.(dec.)

IR (Nujol) : 3400 (shoulder), 3250, 1680 (shoulder), 1635, 1600, 1532, 1450, 1375, 802, 765, 740, 695 cm$^{-1}$ NMR (CDCl$_3$, δ) : 1.63 (3H, s), 4.75 (2H, ABq), 5.00 (1H, broad s), 5.87 (1H, d, J=7.5Hz), 7.1–7.8 (14H, m), 8.19 (1H, d, J=7.5Hz), 10.03 (1H, broad s)

MASS : m/e=465 (M$^+$)

EXAMPLE 11

(1) To a mixture of (3RS)-1,3-dihydro-3-(2-indolylcarbonyl-amino) -5-phenyl-2H-1,4-benzodiazepine-2-one (800 mg), 1-trityl-4-chloromethylimidazole hydrochloride (790 mg) and N,N-dimethylformamide (16 ml) was added sodium hydride (62 % suspension in mineral oil, 168 mg) under stirring and cooling at 0° C. in an ice-bath. The mixture was stirred for 30 minutes at 0° to 5° C. and heated at 70° to 80° C. for 3.0 hours. To the cooled reaction mixture were added acetic acid (2.0 ml) and 6N hydrochloric acid (5 ml). The mixture was stirred for 1.0 hour at 60° C. The cooled reaction mixture was poured into a mixture of ethyl acetate (100 ml) and water (100 ml) under stirring. The organic layer was separated, washed with water three times, dried over magnesium sulfate and evaporated. The residue was chromatographed on silica gel with an eluent of a mixture of chloroform and methanol (20:1) to give (3RS)-1,3-dihydro-3-(2-indolylcarbonylamino) -1-(4-imidazolylmethyl)-5-phenyl-2H-1,4-benzodiazepine-2-one (306.0 mg).

mp: 195° –200° C. (dec.)
IR (Nujol): 3250, 1680, 1635, 1600, 1530 cm$^{-1}$
NMR (CDCl$_3$, δ): 4.93 (2H, s), 5.75 (1H, d, J=8Hz), 6.78 (1H, s), 7.0–7.85 (15H, m), 8.35 (1H, d, J=8Hz), 10.35 (1H, broad s)
MASS: m/e=474 (M$^{+1}$)

The following compounds were obtained according to a similar manner to that of Example 11(1).

(2) (3RS)-1,3-Dihydro-3-(2-indolylcarbonylamino)-1-(4-imidazolylmethyl) -5-(2-fluorophenyl)-2H-1,4-benzodiazepine-2-one
mp : 205° –210° C. (dec.)
NMR (CDC13, 6) : 4.85, 5.10 (2H, A(q, J=15Hz), 5.80 (1H, d, J=8Hz), 6.80–7.83 (15H, m), 8.10 (1H, d, J=8Hz), 10.10 (1H, broad s)
MASS : m/e=492 (M$^{-1}$)

(3) (3RS)-1,3-Dihydro-3-(2-indolylcarbonylamino)-1-[(5-methylimidazol-4-yl)methyl]-5-phenyl-2H-1,4-benzodiazepine-2-one
mp 205° –210° C. (dec.)
NMR (DMSO-d$_6$, δ) : 1.96 (3H, s), 4.80, 5.15 (2H, ABq, J=15Hz), 5.55 (1H, d, J=8Hz), 6.90–8.15 (15H, m), 9.33 (1H, d, J=8Hz), 11.58 (2H, br s)
MASS : m/e=488 (M$^+$)

(4) (3RS)-1,3-Dihydro-3-(2-indolylcarbonylamino)-1-(2-imidazolylmethyl) -5-phenyl-2H-1,4-benzodiazepine-2-one
mp : 175° –180° C. (dec.)
NMR (DMSO-d$_6$, δ) : 5.10 (2H, s), 5.65 (1H, d, J=8Hz), 6.60–8.10 (16H, m), 9.36 (1H, d, J=8Hz), 11.65 (1H, br s), 11.90 (1H, br s)
MASS : m/e=474 (M$^+$)

(5) (3RS)-1,3-Dihydro-3-(2-indolylcarbonylamino)-1-(3-pyrazolylmethyl) -5-phenyl-2H-1,4-benzodiazepine-2-one
mp : 255° –260° C. (dec.)
NMR (DMSO-d$_6$, δ) : 5.03, 5.30 (2H, ABq, J=15Hz), 5.65 (1H, d, J=8Hz), 5.85 (1H, br s), 6.90–7.90 (15H, m), 9.43 (1H, d, J=8Hz), 11.60 (1H, br s), 12.55 (1H, br s),
MASS : m/e=474 (M$^+$)

(6) (3RS)-1,3-Dihydro-3-(2-indolylcarbonylamino)-1-[1,2,4-triazol-3-yl)methyl] -5-phenyl-2H-1,4-benzodiazepine-2-one
mp 205° –210° C. (dec.) 5.66 (1H, d, J=8Hz), 6.90–7.93 (15H, m), 8.23 (1H, br s), 9.40 (1H, d, 0=8Hz), 11.65 (1H, br s)
MASS : m/e=475 (M$^+$)

(7) (3RS)-1,3-Dihydro-3-(2-indolylcarbonylamino)-1[2-(4-imidazolyl)ethyl]-5-phenyl-2H-1,4-benzodiazepine-2-one
mp : 185° –190° C. (dec.)
NMR (DMSO-d$_6$, δ) : 2.63 (2H, t, J=7Hz), 3.85–4.20 (1H, m), 4.20–4.75 (1H, m), 5.55 (1H, d, J=8Hz), 6.60 (1H, s), 6.93–7.85 (15H, m), 9.43 (1H, d, J=8Hz), 11.65 (1H, br s)
MASS : m/e=488 (M$^+$)

EXAMPLE 12

The following compound was obtained according to a similar manner to that of Example 5(1).
(3RS)-1,3-Dihydro-3-(2-indolylcarbonylamino)-1-(2-hydroxyethyl) -5-(2-fluorophenyl)-2H-1,4-benzodiazepine-2-one
IR (Nujol) 3240, 1670, 1630, 1530 cm$^{-1}$
NMR (DMSO-d$_6$, δ) : 3.30–3.90 (2H, m), 3.90–4.40 (1H, m), 4.70–5.0 (1H, m), 5.70 (1H, d, J=8Hz), 6.90–8.0 (13H, m), 9.50 (1H, d, J=8Hz), 11.50 (1H, br s)
MASS : m/e=456(M$^+$)

EXAMPLE 13

The following compounds were obtained according to a similar manner to that of Example 6(1).
(3RS)-1-(2-Acetoxyethyl)-1,3-dihydro-5-(2-fluorophenyl) -3-(2-indolylcarbonylamino)-2H-1,4-benzodiazepine-2-one
NMR (CDCl$_3$, δ) : 1.80 (3H, s), 3.80–4.90 (4H, m), 5.85 (1H, d, J=8Hz), 6.80–7.95 (13H, m), 8.10 (1H, d, J=8Hz), 9.90 (1H, br s)

(2) (3RS)-1-(2-Acetoxyethyl)-1,3-dihydro-3-(2-indolylcarbonylamino) -5-phenyl-2H-1,4-benzodiazepine-2-one
IR (Nujol) : 3250, 1730, 1680, 1600, 1530 cm$^{-1}$
NMR (CDCl$_3$, δ) : 7.65 (3H, s), 4.05–5.0 (4H, m), 5.87 (1H, d, J=8Hz), 7.0–7.85 (14H, m), 8.15 (1H, d, J=8Hz), 10.15 (1H, br s)

(3) (3RS)-1,3-Dihydro-3-(2-indolylcarbonylamino)-1-(2-isopropoxyethyl) -5-phenyl-2H-1,4-benzodiazepine-2-one
mp : 190° –193° C.
NMR (CDCl$_3$, δ) : 0.98 (6H, d, J=6Hz), 3.20–3.70 (3H, m), 3.80–4.40 (2H, m), 5.75 (1H, d, J=8Hz), 7.0–7.80 (14H, m), 8.05 (1H, d, J=8Hz), 9.66 (1H, br s)
MASS m/e=480 (M$^+$)

(4) (3RS)-1,3-Dihydro-3-(2-indolylcarbonylamino)-1-(3-methoxypropyl) -5-phenyl-2H-1,4-benzodiazepine-2-one
mp : 170° –175° C. (dec.)
NMR (CDCl$_3$, δ) : 1.60–1.90 (2H, m), 3.13 (3H, s), 3.05–3.35 (2H, m), 3.40–4.0 (1H, m), 4.25–4.65 (1H, m), 5.73 (1H, d, J=8Hz), 7.0–7.75 (14H, m), 8.06 (1H, d, J=8Hz), 9.60 (1H, br s)
MASS : m/e=466(M$^+$)

(5) (3RS)-1,3-Dihydro-3-(2-indolylcarbonylamino)-1-(2-thienymethyl) -5-phenyl-2H-1,4-benzodiazepine-2-one
NMR (CDCl$_3$, δ) : 5.0, 5.67 (2H, ABq, J=15Hz), 5.80 (1H, d, J=8Hz), 6.70–7.80 (17H, m), 8.10 (1H, d, J=8Hz), 9.80 (1H, br s)
MASS : m/e=490 (M$^+$)

(6) (3RS)-1,3-Dihydro-3-(2-indolylcarbonylamino)-1-furfuryl-5-phenyl -2H-1,4-benzodiazepine-2-one
mp : 150° –155° C. (dec.)
NMR (CDCl$_3$, δ) : 4.96, 5.33 (2H, ABq, J=15Hz), 5.83 (1H, d, J=8Hz), 6.20 (2H, s), 6.95–7.75 (15H, m), 8.10 (1H, d, J=8Hz), 9.90 (1H, br s)
MASS m/e=474 (M$^+$)

(7) (3RS)-1,3-Dihydro-3-(2-indolylcarbonylamino)-1-(2-ethoxyethyl) -5-phenyl-2H-1,4-benzodiazepine-2-one
mp : 205° –210° C. (déc.)
NMR (CDCl$_3$, δ) : 0.96 (3H, t, J=7Hz), 3.35 (2H, q, J=7Hz), 3.50–3.75 (2H, m), 3.80–4.20 (1H, m), 4.20–4.55 (1H, m), 5.80 (1H, d, J=8Hz), 7.05–7.80 (14H, m), 8.10 (1H, d, J=8Hz), 9.90 (1H, br s)

(8) (3RS)-1,3-Dihydro-3-(2-indolylcarbonylamino)-1-(2-methoxyethyl) -5-(2-fluorophenyl)-2H-1,4-benzodiazepine-2-one mp : 230° -235° C. (dec.)

NMR (CDCl$_3$, δ) : 3.20 (3H, s), 3.40-3.75 (2H, m), 3.80-4.16 (1H, m), 4.20-4.55 (1H, m), 5.76 (1H, d, J=8Hz), 6.90-7.80 (13H, m), 8.10 (1H, d, J=8Hz), 9.95 (1H, br s)

MASS m/e=470 (M+)

(9) (3RS)-1,3-Dihydro-3-(2-indolylcarbonylamino)-1-[(2-acetamidothiazol -4-yl)methyl]-5-phenyl-2H-1,4-benzodiazepine-2-one mp 175° -180° C. (dec.)

NMR (CDCl$_3$, δ) : 1.93 (3H, s), 4.83, 5.30 (2H, ABq, J=15Hz), 5.85 (1H, d, J=8Hz), 6.53 (1H, s), 6.90-7.70 (14H, m), 8.25 (1H, d, J=8Hz), 9.56 (1H, s), 10.0 (1H, s)

10 (10) (3RS)-1,3-Dihydro-3-(2-indolylcarbonylamino)-1-(2-bromoethyl) -5-phenyl-2H-1,4-benzodiazepine-2-one NMR (CDCl$_3$, δ) : 3.30-3.70 (2H, m), 3.85-4.40 (1H, m), 4.60-5.20 (1H, m), 5.83 (1H, d, J=8Hz), 7.0-7.90 (14H, m), 8.15 (1H, d, J=8Hz), 10.05 (1H, s)

(11) (3RS)-1,3-Dihydro-1-[[2-(2-tetrahydropyranyl)-3-oxo-2,3-dihydroisoxazol -5-yl]methyl]-3-(2-indolylcarbonylamino) -5-phenyl-1,4-benzodiazepine-2-one IR (Nujol) : 3260, 1700, 1682, 1630 cm$^{-1}$ NMR (CDCl$_3$, δ) : 1.3-2 (6H, m), 3.5-4.2 (2H, m), 4.8-5.6 (4H, ABq), 5.89 (1H, d, J=8Hz), 7.1-7.9 (14H, m), 8.04 (1H, d, J=8Hz), 9.7 (1H, br s)

(12) (3RS)-1,3-Dihydro-3-[(5-chloroindol-2-yl)carbonylamino]-5-phenyl -1-(2-methoxyethyl)-2H-1,4-benzodiazepine-2-one mp : >260° C.

IR (Nujol) : 3350 (sh), 3290, 1668, 1630, 1596, 1530, 1445, 1374, 1324, 1240, 1215, 1110, 910, 759, 690 cm$^{-1}$ NMR (CDCl$_3$, δ) : 3.10 (3H, s), 3.45-3.75 (2H, m), 3.80-4.53 (2H, m), 5.77 (1H, d, J=8.0Hz), 6.9-7.7 (13H, m), 8.12 (1H, d, J=8.0Hz), 10.26 (1H, br s)

MASS : m/e=487 (M+)

(13) (3RS)-1,3-Dihydro-3-[(5-methoxyindol-2-yl)carbonylamino]-5-phenyl -1-(2-methoxyethyl)-2H-1,4-benzodiazepine-2one mp : 221° -222° C.

IR (Nujol) : 3400 (sh), 3250, 1673, 1630, 1596, 1530, 1447, 1375, 1322, 1235, 1115, 1024, 842, 802, 762, 694 cm NMR (CDCl$_3$, δ) : 3.11 (3H, s), 3.45-3.7 (2H, m), 3.82 (3H, s), 3.80-4.55 (2H, m), 5.78 (1H, d, J=8.0Hz), 6.75-7.7 (13H, m), 8.04 (1H, d, J=8.0Hz), 9.90 (1H, br s)

MASS : m/e=482 (M +)

(14) (3RS)-1-(3-Bromopropyl)-3-(2-indolylcarbonylamino)-5-phenyl -1,3-dihydro-2H-1,4-benzodiazepine-2-one IR (Nujol) : 3400 (sh), 3250, 1675, 1633, 1600, 1530, 1445, 1375, 1242, 800, 742, 692 cm$^{-1}$ NMR (CDCl$_3$, δ) : 1.8-2.3 (2H, m), 2.95-3.4 (2H, m), 3.8-4.75 (1H, dt, J=13.8Hz, 6.6Hz), 4.35-4.65 (1H, dt, J=13.8Hz, 6.6Hz), 5.77 (1H d, J=8Hz), 7.0-7.7 (14H, m), 8.15 (1H, d, J=8Hz), 9.97 (1H, br s)

EXAMPLE 14

A mixture of (3RS)-1,3-dihydro-3-(2-indolylcarbonyl-amino) -1-[(2-acetamidothiazol-4-yl)methyl]-5-phenyl-2H-1,4-benzodiazepine -2-one, methanol (13 ml), tetrahydrofuran (8 ml) and conc. hydrochloric acid (0.8 ml) was stirred for 7.0 hours at 70° C., cooled and adjusted to pH 7.0 with aqueous solution of sodium bicarbonate. To the mixture were added water (100 ml) and ethyl acetate (100 ml) under cooling. The separated organic layer was washed with water, dried over magnesium sulfate and evaporated. The residue was chromatographed on silica gel with an eluent of a mixture of ethyl acetate and chloroform (2:1) to give (3RS)-1,3-dihydro-3-(2-indolylcarbonylamino) -1-[(2-amino-thiazol-4-yl)methyl]-5-phenyl -2H-1,4-benzodiazepine-2-one.

mp : 200° -205° C. (dec.)

NMR (DMSO-d$_6$, δ) : 4.80, 5.06 (2H, ABq, J=15Hz), 5.60 (1H, d, J=8Hz), 6.06 (1H, s), 6.75 (2H, br s), 6.90-7.95 (14H, m), 9.40 (1H d, J=8Hz), 11.65 (1H, s)

MASS : m/e=506 (M+)

EXAMPLE 15

(1) A mixture of (3RS)-1,3-dihydro-3-(2-indolylcarbonyl-amino -1-[(E)-3-methoxycarbonyl-2-propenyl]-5-phenyl-2H-1,4-benzodiazepine -2-one (0.47 g), tetrahydrofuran (15 ml), methanol (7.5 ml) and 1N aqueous sodium hydroxide (1 ml) was stirred for 1.0 hour at room temperature and cooled. To the cooled reaction mixture were added water (100 ml) and ethyl acetate (100 ml) and the mixture was adjusted to pH 4.0 with 6N hydrochloric acid under stirring. The organic layer was separated, washed with water, dried over magnesium sulfate and evaporated. The residue was chromatographed on silica gel with an eluent of a mixture of chloroform and methanol (1:1) to give (3RS)-1,3-dihydro-3-(2-indolylcarbonylamino)-1-[(E)-3-carboxy-2-propenyl]-5-phenyl-2H-1,4-benzodiazepine-2-one (80 mg).

mp : 175° -180° C. (dec.)

NMR (DMSO-d$_6$, δ) : 3.13 (2H, d, J=7.5Hz) 5.20-5.66 (1H, m), 5.66 (1H, d, J=8Hz), 6.90-7.90 (15H, m), 9.55 (1H, d, J=8Hz), 11.58 (1H, br s)

MASS : m/e=478 (M+)

The following compound was obtained according to a similar manner to that of Example 15(1).

(2) (3RS)-1,3-Dihydro-3-(2-indolylcarbonylamino)-1[(Z)-3-carboxy-2-propenyl]-5-phenyl-2H-1,4-benzodiazepine-2-one mp : 230° -235° C. (dec.)

NMR (DMSO-d$_6$, δ) : 5.12 (2H, d, J=4.5Hz), 5.68 (1H, d, J=8Hz), 5.75-6.30 (1H, m), 6.95-7.90 (15H, m), 9.55 (1H, d, J=8Hz)

MASS : m/e=478 (M+)

EXAMPLE 16

A mixture of (3RS)-1,3-dihydro-3-(2-indolylcarbonylamino) -1-(2-bromoethyl)-5-phenyl-2H-1,4-benzodiazepine-2-one (0.3 g) and 1-methylpiperazine (3.0 ml) was stirred for 4.0 hours at room temperature aND diisopropyl ether (20 ml) was added thereto. The resultant precipitates were collected by filtration and dissolved in diluted hydrochloric acid. The solution was adjusted to pH 7 with an aqueous solution of sodium bicarbonate and the resultant precipitates were collected by filtration to give (3RS)-1,3-dihydro-3-(2-indolylcarbonylamino)-1-[2-(4-methyl-1-piperazinyl)ethyl]-5-phenyl-2H-1,4-benzodiazepine-2-one (0.20 g).

mp : 135° -140° C. (dec.)

IR (Nujol) : 3230, 1670, 1635, 1600, 1530 cm$^{-1}$

NMR (CDCl$_3$, δ) : 2.20-2.70 (13H, m), 3.60-4.10 (1H, m), 4.30-4.90 (1H, m), 5.83 (1H, d, J=8Hz), 7.0-7.90 (14H, m), 8.20 (1H, d, J=8Hz), 10.10 (1H, br s)

EXAMPLE 17

A mixture of (3RS)-1-formylmethyl-3-(2-indolyl-carbonylamino) -5-phenyl-1,3-dihydro-2H-1,4-benzodiazepine-2-one (0.5 g) and methoxyamine hydrochloride (144.1 mg) in ethanol (5 ml) was stirred for 3 hours at room temperature. After removal of the solvent, to the residue were added ethyl acetate and a diluted aqueous solution of sodium bicarbonate. The organic layer was washed with water twice and dried over magnesium sulfate. Removal of the solvent afforded an amorphous material (0.56 g), which was subjected to column chromatography on silica gel eluting with a mixture of chloroform and ethyl acetate (10:1). The fractions containing the desired product were combined and evaporated to give a glassy material, which was stirred in diisopropyl ether overnight to afford (3RS)-1-(2-methyxyiminoethyl)-3-(2-indolylcarbonylamino) -5-phenyl-1,3-dihydro-2H-1,4-benzodiazepine -2-one (1:1 mixture of E- and Z-isomers, 0.34 g) as white powder.

mp: 169° -174° C.

IR (Nujol) : 3400 (sh), 3300, 1690, 1640, 1600, 1535, 1490, 1450, 1379, 1040, 850, 820, 772, 747, 699 cm$^{-1}$ NMR (CDCl$_3$, δ) : 3.72 and 3.87 (3H, each s), 4.6-4.7 and 4.75-4.85 (2H, each dd, J=5.4Hz, 3Hz), 5.80 (1H, d, J=8Hz), 6.62 and 7.05 (1H, each t, J=5.4Hz), 7.07-7.7 (14H, m), 8.03 (1H, d, J=8Hz), 9.78 (1H, br s)

MASS : m/e=465 (M+)

EXAMPLE 18

To a suspension of (3RS)-1,3-dihydro-1-[[2-(2-tetrahydropyranyl) -3-oxo-2,3-dihydroisoxazol-5-yl]methyl]-3-(2- indolylcarbonylamino) -5-phenyl-1,4-benzodiazepine-2-one (212.9 mg) in methanol (4 ml) was added 2N hydrochloric acid under stirring at room temperature. Tetrahydrofuran (1 ml) was added thereto in order to gain a clear solution, which was stirred at the same temperature for 30 minutes. The reaction mixture was evaporated to dryness to afford yellow powder, which was washed with ether by stirring overnight, collected by filtration and dried to give (3RS)-1,3-dihydro-1-[(3-hydroxyisoxazol-5-yl)methyl]-3-(2-indolylcarbonylamino) -5-phenyl-1,4-benzodiazepine-2-one (149.1 mg) as yellow powder.

mp : 207° C. (dec.)

NMR (DMSO-d$_6$, δ) : 5.24 (2H, ABq, J=15Hz, 25.5Hz), 5.67 (1H, d, J=8Hz), 5.70 (1H, s), 7.0-7.85 (14H, m), 9.52 (1H, d, J=8Hz), 11.61 (1H, broad s)

MASS : m/e=491 (M+)

EXAMPLE 19

The following compounds were obtained according to a similar manner to that of Example 6(1).

(1) (3RS)-1-[2-(2-Chloroethyoxy]-1,3-dihydro-3-(2-indolylcarbonylamino) -5-phenyl-2H-1,4-benzodiazepine-2-one NMR (CDCl$_3$, δ) : 3.20-4.60 (8H, m), 5.80 (1H, d, J=8Hz), 7.0-7.80 (14H, m), 8.15 (1H, d, J=8Hz), 10.20 (1H, br s)

(2) (3RS)-1-(2-Vinyloxyethyl)-1,3-dihydro-3-(2-indolylcarbonylamino) -5-phenyl-2H-1,4-benzodiazepine-2-one mp : 210° -215° C. (dec.)

NMR (CDCl$_3$, δ): 3.75-4.0 (4H, m), 4.0-4.20 (1H, m), 4.30-4.65 (1H, m), 5.76 (1H, d, J=8Hz), 6.05-6.35 (1H, m), 7.0-7.75 (14H, m), 8.03 (1H, d, J=8Hz), 9.53 (1H, br s)

MASS : m/e=464 (M+)

(3) (3RS)-1-(2-Benzyloxyethyl)-1,3-dihydro-3-(2-indolyl-carbonylamino) -5-phenyl-2H-1,4-benzodiazepine-2-one mp : 195° -200° C. (dec.)

NMR (CDCl$_3$, δ) : 3.55-3.80 (2H, m), 3.80-4.20 (1H, m), 4.20-4.55 (1H, m), 4.30 (2H, s), 5.75 (1H, d, J=8Hz), 6.96-7.80 (14H, m), 8.06 (1H, d, J=8Hz), 9.85 (1H, br s)

(4) (3RS)-1-(3,4-Dimethoxybenzyl)-1,3-dihydro-3-(2-indolylcarbonylamino) -5-phenyl-2H-1,4-benzodiazepine-2-one mp : 220° -225° C. (dec.)

IR (Nujol) : 3300, 3200, 1680, 1635, 1590, 1525, 1505 cm$^{-1}$

NMR (CDCl$_3$, δ) : 3.40 (3H, s), 3.75 (3H, s), 4.70, 5.75 (2H, ABq, J=15Hz), 5.90 (1H, d, J=8Hz), 6.45-6.65 (3H, m), 7.10-7.80 (14H, m), 8.20 (1H, d, J=8Hz), 9.98 (1H, br s)

(5) (3RS)-1-(3,4-Diacetoxybenzyl)-1,3-dihydro-3-(2-indolylcarbonylamino) -5-phenyl-2H-1,4-benzodiazepine-2-one (6) (3RS)-1-Benzyl-1,3-dihydro-3-(2-indolylcarbonylamino) -5-phenyl-2H-1,4-benzodiazepine-2-one mp : 145-150° C. (dec.)

IR (Nujol) : 3250, 1680, 1635, 1600, 1530 cm$^{-1}$

NMR (CDCl$_3$, δ) : 4.88, 5.68 (2H, ABq, J=15Hz), 5.93 (1H, d, J=5Hz), 7.0-7.80 (19H, m), 8.25 (1H, d, J=8Hz), 10.08 (1H, br s)

MASS : m/e =484 (M+)

(7) (3RS)-1-(2-Phthalimidoethyl)-1,3-dihydro-3-(2-indolylcarbonylamino) -5-phenyl-2H-1,4-benzodiazepine-2-one IR (Nujol) : 3400, 3250, 1770, 1712, 1678, 1646 cm$^{-1}$ NMR (DMSO$_6$, δ) : 3.6-4.8 (4H, m), 5.60 (1H, d, J=8Hz), 7.0-8.0 (18H, m), 9.50 (1H, d, J=8Hz), 11.45 (1H, broad s)

(8) (3RS)-1-(2-Methylthioethyl)-1,3-dihydro-3-(2indolylcarbonylamino) -5-phenyl-2H-1,4-benzodiazepine-2-one mp 149-156° C.

IR (Nujol) : 3380 (sh.), 3270, 1672, 1635, 1595, 1530, 1445, 1375, 1320, 740, 690 cm$^{-1}$ NMR (CDCl$_3$, δ) : 1.98 (3H, s), 2.63 (2H, t, J=7.5Hz), 3.88 (1H, dt, J=13.5Hz, 7.5Hz), 4.63 (1H, dt, J=13.5Hz , 7.5Hz), 5.80 (1H, d, J=8.4Hz), 7.0-7.8 (14H, m), 8.11 (1H, d, J=8.4Hz), 9.93 (1H, br s)

MASS : m/e =469 (M+)

EXAMPLE 20

A mixture of (3RS)-1-(3,4-diacetoxybenzyl)-1,3-dihydro-3-(2-indolylcarbonylamino) -5-phenyl-2H-1,4-benzodiazepine-2-one (287 mg), methanol (5 ml), tetrahydrofuran (5 ml), water (1 ml) and 1N aqueous potassium carbonate (5 ml) was stirred for 1.0 hour at 0 - 5° C. and then adjusted to pH 1-2 with 6N hydrochloric acid. Ethyl acetate (50 ml) and water (50 ml) were added to the mixture under stirring. The separated organic layer was washed with water, dried over magnesium sulfate and evaporated. The residue was chromatographed on silica gel with an eluent of a mixture of chloroform and ethyl acetate (4:1) to give (3RS)-1(3,4-dihydroxybenzyl) -3-(2-indolylcarbonylamino)-5-phenyl-2H-1,4-benzodiazepine-2-one (155 mg).

mp 165-170° C. (dec.)

NMR (CDCl$_3$-DMSO-d$_6$, δ) : 4.75, 5.35 (2H, ABq, J=15Hz), 5.75(1H, d, J=8Hz), 6.20-6.60 (3H, m), 6.90–7.70 (14H, m), 8.35 (2H, br s), 8.96 (1H, d, J=8Hz), 11.46 (1H, br s)

MASS : m/e =516 (M+)

EXAMPLE 21

To a solution of carbon tetrachloride (792.1 mg) in methylene chloride (20 ml) was added triphenylphosphine (2.70 g) under stirring at room temperature. To the resultant mixture was added (3RS)-1-formylmethyl-1,3-dihydro-3-(2-indolylcarbonylamino) -5-phenyl-2H-1,4-benzodiazepine-2-one (0.90 g). The mixture was stirred for 6 hours under stirring at room temperature. From the reaction mixture, methylene chloride was removed by evaporation. Water was added to the residue. The mixture was acidified with dilute hydrochloric acid and extracted with ethyl acetate twice. The extract was dried over magnesium sulfate and evaporated to give an red oil, which was subjected to column chromatography on silica gel with an eluent of a mixture of chloroform and ethyl acetate (20:1). The fractions containing the objective compound were combined and evaporated to dryness to give a glassy material (0.20 g), which was pulverized in diisopropyl ether to give (3RS)-1-(3,3-dichloro-2-propenyl)-1,3-dihydro-3-(2-indolylcarbonylamino)-5-phenyl -2H-1,4-benzodiazepine2-one (138.8 mg) as yellow powder.

mp : 149–152° C. (dec.)

IR (Nujol) : 3400 (sh.), 3550, 1680, 1640, 1535, 1450, 1378, 742, 694 cm$^{-1}$

NMR (CDCl$_3$, δ) : 4.53 (1H, dd, J=15Hz, 7.2Hz), 4.77 (1H, dd, J=15Hz, 7.2Hz), 5.93 (1H, dd, J=7.2Hz, 7.8Hz), 5.77 (1H, d, J=7.8Hz), 7.0 -7.7 (14H, m), 7.99 (1H, d, J=7.8Hz), 9.67 (1H, br s)

MASS : m/e =503 (M+)

EXAMPLE 22

The following compound was obtained according to a similar manner to that of Example 16.

(3RS)-1-[2-(2-hydroxyethylamino)ethyl]-1,3-dihydro-3-(2-indolylcarbonylamino) -5-phenyl-2H-1,4-benzodiazepine-2-one mp : 125–130° C. (dec.)

IR (Nujol) : 3250, 1680, 1630, 1600, 1535 cm$^{-1}$

NMR (CDCl$_3$δ) : 2.45–2.85 (4H, m), 3.30–3.50 (2H, m), 3.50–3.90 (1H, m), 4.20–4.60 (1H, m), 5.80 (1H, d, J=8Hz), 7.0–7.80 (14H, m), 8.25 (1H, d, J=8Hz), 10.20 (1H, br s)

EXAMPLE 23

A mixture of (3RS)-1-[2-(2-chloroethoxy)ethyl]-1,3-dihydro-3-(2-indolylcarbonylamino) -5-phenyl-2H-1,4-benzo-diazepine-2-one (700 mg), potassium phthalimide (610 mg) and N,N-dimethylformamide (5 ml) was stirred for 7 hours at 80–90° C. The reaction mixture was poured into a cold water (100 ml) and extracted with ethyl acetate. The extract was washed with water, dried over magnesium sulfate and evaporated to give (3RS)-1-[2-(2-phthalimidoethoxy) ethyl]-1,3-dihydro-3-(2-indolylcarbonylamino)-5-phenyl-2H-1,4-benzodiazepine-2-one (0.9 g).

EXAMPLE 24

A mixture of (3RS)-1-[2-(2-chloroethoxy)ethyl]-1,3-dihydro-3-(2-indolylcarbonylamino) -5-phenyl-2H-1,4-benzodiazepine-2-one (500 mg) and 1-methylpiperazine (5.0 ml) was stirred at 70° C. for 5.0 hours. Then diisopropyl ether (30 ml) was added to the reaction mixture. After the resultant precipitate was filtered off, the filtrate was evaporated. The residue was washed with water and dried to give (3RS)-1-[2-[2-(4-methyl-1-piperazinyl)ethoxy]ethyl]-1,3-dihydro-3-(2-indolylcarbonylamino)-5-phenyl-2H-1,4-benzodiazepine-2-one (0.43 g).

mp : 100–105° C. (dec.)

IR (Nujol) : 3250, 1690, 1635, 1600, 1540 cm$^{-1}$ (CDCl$_3$, δ) : 2.15–2.60 (13H, m), 3.35–4.50 (6H, m), 5.80 (1H, d, J=8Hz), 7.0–7.85 (14H, m), 8.15 (1H, d, J=8Hz), 10.10 (1H, br s)

MASS : m/e =564 (M+)

EXAMPLE 25

(1) A mixture of (3RS)-1-(2-phthalimidoethyl)-1,3-dihydro-3-(2-indolylcarbonylamino) -5-phenyl-2H-1,4-benzodiazepine-2-one (1.04 g) and hydrazine hydrate (130 mg) in N,N-dimethylformamide (10 ml) was heated at 70° C. under stirring for 3 hours. Additional hydrazine hydrate (130 mg) was added thereto. The resultant mixture was heated at 80° C. for 12.5 hours. The mixture was poured into water and extracted with ethyl acetate. The extract was washed with water and dried. The solvent was removed by evaporation under reduced pressure to afford a viscous oil (1.03 g), which was purified by column chromatography on silica gel with an eluent of a mixture of chloroform and methanol (50:1). The fractions containing the desired product were combined and evaporated to give (3RS)-1-(2-aminoethyl)-1,3-dihydro-3-(2-indolylcarbonylamino) -5-phenyl-2H-1,4-benzodiazepine-2-one (0.76 g) as an amorphous oil, which was pulverized in ether by stirring overnight to give crystalline powder (456.2 mg).

IR (Nujol) : 3260, 1690, 1660, 1620 cm$^{-1}$

NMR (CDCl$_3$, δ) : 3.3–3.8 (3H, m), 4.0–4.4 (1H, m), 5.83 (1H, d, J=8Hz), 6.12 (2H, broad t), 7.1–7.9 (14H, m), 8.20 (1H, d, J=8Hz), 9.85 (1H, broad s)

The following compound was obtained according to a similar manner to that of Example 25(1).

(2) (3RS)-1-[2-(2-Aminoethoxy)ethyl]-1,3-dihydro-3-(2-indolylcarbonylamino) -5-phenyl-2H-1,4-benzodiazepine-2-one.

mp : 130–135° C. (dec.)

IR (Nujol) : 3250, 1680, 1640, 1600, 1540 cm$^{-1}$

NMR (CDCl$_3$, δ) : 2.30–2.80 (2H, m), 3.0–4.0 (5H, m), 4.30–4.70 (1H, m), 5.80 (1H, s), 7.0–7.80 (14H, m)

MASS m/e=481 (M+)

EXAMPLE 26

A mixture of a mixture (0.66 g) of (3R)-1-[2-((2R)-2-tert-butoxycarbonylamino-2-benzhydryloxycarbonylethylthio)ethyl]-1,3-dihydro-3-(2-indolylcarbonylamino) -5-phenyl-2H-1,4-benzodiazepine-2-one and (3S)-1-[2-((2R)-2-tert-butoxycarbonylamino-2benzhydryloxycarbonylethylthio)ethyl]-1,3-dihydro-3-(2-indolylcarbonylamino) -5-phenyl-2H-1,4-benzodiazepine-2-one, anisole (0.6 ml), trifluoroacetic acid (1.5 ml) and dichloromethane (15 ml) was stirred for 3.0 hours at room temperature. After removal of the solvent, the residue was mixed with ethyl acetate (50 ml) and water (50 ml). The mixture was adjusted to pH 6-7 with 5% aqueous solution of sodium bicarbonate under stirring. The organic layer was separated and concentrated. The resultant precipitate was collected by filtration, washed with water and dried to give a mixture (0.20 g) of (3R)-1-[2-((2R)-2-amino-2-carboxyethylthio)ethyl]-1,3-dihydro -3-(2-indolylcarbonylamino -5-phenyl-2H-1,4-benzodiazepine-2-one and (3S)-1-[2-((2R)-2-amino-2-carboxyethylthio) ethyl]-1,3-dihydro-3-(2-indolylcarbonylamino) -5-phenyl-2H-1,4-benzodiazepine-2-one.

mp : 190–195° C. (dec.)

NMR (CD$_3$OD+DCl, δ) : 2.60–3.10 (4H, m), 4.0–4.40 (2H, m), 4.60–5.0 (1H, m), 5.96 (1H, s), 6.65–8.15 (14H, m)

MASS : m/e =541 (M+)

EXAMPLE 27

A mixture of (3RS)-1-[N-(ethoxycarbonylmethyl)-carbamoylmethyl]-1,3-dihydro-3-(2-indolylcarbonylamino) -5-phenyl-2H-1,4-benzodiazepine-2-one (350 mg), tetrahydrofuran (10 ml) and 1N aqueous sodium hydroxide (0.65 ml) was stirred for 4.0 hours at room temperature, and then water (50 ml) and ethyl acetate (50 ml) were added thereto. The mixture was adjusted to pH 1-2 with 1N hydrochloric acid under stirring. The separated organic layer was washed with water, dried over magnesium sulfate and evaporated. The residue was crystallized with tetrahydrofuran to give (3RS)-1-[N-(carboxymethyl)carbamoylmethyl]-1,3-dihydro-3-(2-indolylcarbonylamino) -5-phenyl-2H-1,4-benzodiazepine-2-one (204 mg).

mp : 170–175° C. (dec.)

NMR (DMSO-d$_6$, δ) : 3.77 (2H, d, J=5Hz), 4.65 (2H, s), 5.73 (1H, d, J=8Hz), 6.90–7.80 (14H, m), 8.50 (1H, tri, J=5Hz), 9.45 (1H, d, J=8Hz), 11.65 (1H, br s)

EXAMPLE 28

(1) To a mixture of (3RS)-1-carboxymethyl-1,3-dihydro-3-(2-indolylcarbonylamino) -5-phenyl-2H-1,4-benzodiazepine-2-one (452 mg), 1-hydroxybenzotriazole (135 mg) and N,N-dimethylformamide (5 ml) was added N,N'-dicyclohexylcarbodiimide (206 mg) at 5° C. under stirring. The mixture was stirred for 1.0 hour at room temperature, and glycinamide hydrochloride (74 mg) and triethylamine (120 mg) were added to the reaction mixture at 5° C. The mixture was stirred for 3.0 hours at room temperature. The precipitates were filtered off and the filtrate was poured into a mixture of ethyl acetate and water. The resultant precipitates were collected by filtration to give (3RS)-1-[N-(carbamoylmethyl)carbamoylmethyl]-1,3-dihydro-3-(2-indolylcarbonylamino)-5-phenyl-2H-1,4-benzodiazepine-2-one (180 mg).

IR (Nujol) : 3270, 1680, 1665, 1630, 1600, 1540 cm$^{-1}$

NMR (DMSO-d$_6$, δ) : 3.65 (2H, d, J=5Hz), 4.65 (2H, s), 5.73 (1H, d, J=8Hz), 6.90–7.80 (14H, m), 8.40 (1H, tri, J=5Hz), 9.48 (1H, d, J=8Hz), 11.65 (1H, s)

MASS : m/e =508 (M+)

The following compounds were obtained according to a similar manner to that of Example 28(1).

(2) (3RS)-1-[N-(ethoxycarbonylmethyl)carbamoylmethyl]-1,3-dihydro-3-(2-indolylcarbonylamino) -5-phenyl-2H-1,4-benzodiazepine-2-one (3) Mixture of (3R)-1-[N-((1S)-1-carbamoyl-2-phenylethyl)carbamoylmethyl]-1,3-dihydro-3-(2-indolylcarbonylamino) -5-phenyl-2H-1,4-benzodiazepine-2-one and (3S)-1-[N-((1S)-1-carbamoyl-2-phenylethyl)carbamoylmethyl]-1,3-dihydro-3-(2-indolylcarbonylamino) -5-phenyl-2H-1,4-benzodiazepine-2-one mp : 165–170° C. (dec.)

IR (Nujol) : 3230, 1680, 1650, 1600, 1525 cm$^{-1}$

NMR (DMSO-d$_6$, δ: 2.65–3.20 (2H, m), 4.30–4.90 (3H, m), 5.67 (1H, d, J=8Hz), 7.0–7.80 (19H, m), 8.25–8.50 (1H, m), 9.37–9.57 (1H, m), 11.65 (1H, br s)

MASS : m/e =598 (M+)

EXAMPLE 29

To a suspension of (3RS)-1-carboxymethyl-1,3-dihydro-3-(2-indolylcarbonylamino) -5-phenyl-2H-1,4-benzodiazepine-2-one (1.53 g) in methylene chloride (30 ml) was added oxalyl chloride (1.29 g) under stirring and cooling in an ice-bath. The mixture was stirred for 3.5 hours at room temperature. The solvent and the excess oxalyl chloride were removed under reduced pressure and the residue was triturated in ether to give an acid chloride as an orange powder, which was collected by filtration, washed with ether and dried under reduced pressure. The powder (0.5 g) was added to a solution of cyanoamine (0.17 g) and triethylamine (0.42 g) in methylene chloride (20 ml) under stirring at room temperature. The mixture was stirred for 2 hours at the same temperature. To the reaction mixture was added methylene chloride (50 ml) and the mixture was washed with dilute hydrochloric acid and water. After being dried over magnesium sulfate, the organic layer was evaporated under reduced pressure. The residue was subjected to a column chromatography on silica gel with an eluent of a mixture of ethyl acetate, n-hexane and acetic acid (2:1:0.1) to give the desired product, which was stirred in ether to give (3RS)-1-[N-(cyano)-carbamoylmethyl]-1,3-dihydro-3-(2-indolylcarbonylamino)-5-phenyl-2H-1,4-benzodiazepine-2-one as a light orange powder (0.14 g).

mp : 255–260° C. (dec.)

IR (Nujol) : 2170, 1680, 1640, 1600, 1540, 1460, 1380, 1305, 745 cm$^{-1}$

NMR (DMSO-d$_6$, δ) : 4.77 (2H, S), 5.75 (1H, d, J=8Hz), 7.0–7.9 (14H, m), 9.52 (1H, d, J=8Hz), 11.50 (1H, broad s)

EXAMPLE 30

To a solution of (3RS)-1-(3-bromopropyl)-1,3-dihydro-3-(2-indolylcarbonylamino) -5-phenyl-2H-1,4-benzodiazepine-2-one (0.52 g) in N,N-dimethylformamide (3 ml) was added methanolic sodium methanethiolate prepared from 30% methanolic methanethiol (0.48 g) and 1M methanolic sodium hydroxide (3.0 ml). The mixture was stirred for 6 hours and allowed to stand for 37 hours.

The reaction mixture was poured into water containing several drops of acetic acid under stirring and extracted with ethyl acetate twice, and the extracts were combined, washed with water three-times and dried over magnesium sulfate. The solvent was evaporated to dryness to afford yellow oil (0.59 g) which was subjected to column chromatography on silica gel with an eluent of a mixture of chloroform and ethyl acetate (20:1) to give a glassy material (330 mg). This material was stirred in diisopropyl ether overnight to give (3RS)-1-(3-methylthiopropyl)-1,3-dihydro-3-(2indolylcarbonylamino) -5-phenyl-2H-1,4-benzodiazepine-2-one (248.1 mg) as a white powder.

mp : 216–221° C.

IR (Nujol) : 3430, 3260, 1673, 1638, 1600, 1532, 1450, 1375, 1270, 800, 778, 739, 695 cm$^{-1}$ NMR (CDCl$_3$, δ) : 1.7–2.0 (2H, m), 1.9 (3H, s), 2.25–2.45 (2H, m), 3.7–4.0 (1H, dt, J=13.8Hz, 6.6Hz), 4.4–4.7 (1H, dt, J=13.8Hz , 6.6Hz), 5.83 (1H, d, J=7.8Hz), 7.1–7.8 (14H, m), 8.17 (1H, d, J=7.8Hz), 10.01 (1H, br s)

MASS : m/e =482 (M+)

EXAMPLE 31

(1) A mixture of (3RS)-1-(2-bromoethyl)-1,3-dihydro-3-(2-indolylcarbonylamino) -5-phenyl-2H-1,4-benzodiazepine-2-one (501 mg), triethylamine (0.12 g), 4-mercarptopyridine (0.133 g) and N,N-dimethylformamide (6 ml) was stirred overnight at room temperature. The reaction mixture was poured into a mixture of water and ethyl acetate. The organic layer was separated, washed with water three times, dried over magnesium sulfate and evaporated. The residue was chromatographed on silica gel with an eluent of ethyl acetate to give 3RS)-1-[2-(4-pyridylthio)ethyl]-1,3-dihydro-3-(2-indolylcarbonylamino) -5-phenyl-2H-1,4-benzodiazepine-2-one (0.19 g).

mp : 150–155° C. (dec.)

IR (Nujol) : 3230, 1680, 1630, 1600, 1570, 1530 cm$^{-1}$

NMR (CDCl$_3$, δ) : 3.0 3.30 (2H, m), 3.70-4.10 (1H, m), 4.40–4.80 (1H, m), 5.80 (1H, d, J=8Hz), 7.0–7.80 (16H, m), 8.10 (1H, d, J=8Hz), 8.25–8.45 (2H, m), 10.05 (1H, br s)

MASS : m/e =531 (M+)

The following compound was obtained according to a similar manner to that of Example 31(1).

(2) Mixture of (3R)-1-[2-((2R)-2-tert-butoxycarbonylamino -2-benzhydryloxycarbonylethylthio)ethyl]-1,3-dihydro-3-(2-indolylcarbonylamino) -5-phenyl-2H-1,4-benzodiazepine-2-one and (3S)-1-[2-((2R)-2-tert-butoxycarbonylamino-2-benzhydryloxycarbonylethylthio)ethyl]-1,3-dihydro-3-(2-indolylcarbonylamino)-5-phenyl-2H-1,4-benzodiazepine-2-one.

NMR (CDCl$_3$, δ: 1.40 (9H, s), 2.20–3.10 (4H m), 3.50–4.0 (1H, m), 4.20–4.70 (2H, m), 5.15–5.45 (1H, m), 5.80 (1H, d, J=8Hz), 6.90 (1H, s), 7.10–7.85 (24H, m), 8.15 (1H, d, J=8Hz), 9.75 (1H, br s)

EXAMPLE 32

To a solution of (3RS)-1-(2-aminoethyl)-1,3-dihydro-3-(2-indolylcarbonylamino) -5-phenyl-2H-1,4-benzodiazepine-2-one (434 mg) and triethylamine (222 mg) in methylene chloride (4 ml) was dropwise added acetyl chloride (172.8 mg) under cooling in ice-water bath and stirring. The mixture was stirred for 4 hours under the same conditions. After the solvent was removed by evaporation under reduced pressure, water was added to the residue. The mixture was extracted with ethyl acetate. The extract was washed with an aqueous sodium bicarbonate solution and water, then dried over magnesium sulfate. The solvent was removed by evaporation to afford a brown oil (672.2 mg), which was chromatographed on silica gel with an eluent of a mixture of chloroform and methanol (30:1). The fractions containing the desired product were combined and evaporated to give an amorphous product, which was pulverized in ether by stirring overnight. The crystalline powder was collected by filtration and washed with ether to give (3RS)-1-(2-acetylaminoethyl)-1,3-dihydro-3-(2-indolylcarbonylamino) -5-phenyl-2H-1,4-benzodiazepine-2-one (327.1 mg).

mp : 167–175° C. (dec.)

IR (Nujol) : 3250, 1690, 1672, 1635 cm$^{-1}$

NMR (DMSO-d$_6$, δ) : 2.25 (3H, s), 3.6–4.4 (4H, m), 5.59 (1H, d, J=8Hz), 6.9–7.9 (14H, m), 9.48 (1H, d, J=8Hz), 11.48 (1H, broad s)

MASS : m/e =479 (M+)

PREPARATION 10

To a suspension of (3RS)-1,3-dihydro-5-(2-fluorophenyl)-3-phthalimido -2H-1,4-benzodiazepine-2-one (1.0 g) and 1-trityl-4-chloromethylimidazole hydrochloride (1.28 g) in N,N-dimethylformamide (25 ml) was added sodium hydride (40% suspension in mineral oil, 0.36 g) gradually under stirring and cooling in an ice-bath, and the mixture was stirred at the same temperature for one hour and then at ambient temperature for 17 hours. After addition of acetic acid (0.5 ml), the reaction mixture was poured into water (100 ml). The mixture was adjusted to pH 7 with an aqueous sodium bicarbonate under stirring. The resultant precipitates were collected by filtration, washed with water and dried under reduced pressure and warming to give yellow powder (2.22 g). The powder was purified by column chromatography on silica gel with an eluent of a mixture of chloroform and ethyl acetate (20:1) to afford (3RS)-1,3-dihydro-5-(2-fluorophenyl)-3-phthalimido--1-(1-trityl-4-imidazolyl)methyl -2H-1,4-benzodiazepine-2-one (1.38 g).

NMR (DMSO-d$_6$, δ) : 5.08 (2H, ABq), 5.75 (1H, s), 6.7–7.7 (29H, m)

PREPARATION 11

To a suspension of (3RS)-1,3-dihydro-5-(2-fluorophenyl) -3-phthalimido -1-(1-trityl-4-imidazolyl)methyl-2H-1,4-benzodiazepine-2-one (19.96 g) in tetrahydrofuran (200 ml) was added a solution of hydrazine hydrate (1.38 g) in methanol (10 ml). The mixture was stirred at ambient temperature for 0.5 hour and then the resultant clear solution was refluxed for 2 hours under stirring. The reaction mixture was cooled in an ice-bath and the precipitates were filtered off. The filtrate and washings were evaporated under reduced pressure. The residue was dissolved in chloroform and the mixture was filtered. The filtrate was evaporated to give an oil (19.30 g), which was chromatographed on silica gel with an eluent of a mixture of chloroform and methanol (30:1) to afford (3RS)-1,3-dihydro-5-(2-fluorophenyl)-3-amino-1(1-trityl-4-imidazolyl)methyl -2H-1,4-benzodiazepine-2-one (9.97 g).

NMR (CDCl$_3$, δ) : 2.42 (2H, broad s), 4.49 (1H, s), 5.06 (2H, s), 6.8–8.0 (25H, m)

PREPARATION 12

(1) To a solution of (3RS)-1,3-dihydro-5-(2-fluorophenyl) -3-amino-1-(1-trityl-4-imidazolyl)methyl-2H-1,4-benzodiazepine-2-one (591.7 mg) in ethyl acetate (2 ml) was added a solution of (S)-(+)-mandelic acid (129.3 mg) in ethyl acetate (4 ml) under stirring at ambient temperature. The precipitated gel was dissolved by addition of methanol (0.2 ml). To the clear solution were added ethyl acetate (4 ml) and diisopropyl ether (three drops). The mixture was stirred for 2 hours and allowed to stand overnight. The resultant precipitates were collected by filtration, washed with ethyl acetate and diisopropyl ether and dried to give white powder (202.2 mg), which was recrystallized from ethyl acetate to afford (S)-(+)-mandelic acid salt of (3S)-1,3-dihydro-5-(2-fluorophenyl) -3-amino-1-(1-trityl-4-imidazolyl)methyl2H-1,4-benzodiazepine -2-one as crystals.

[α]$_D^{24}$= −33.33° (C=0.846, CH$_3$OH)

Further, a mixture of (3R)-1,3-dihydro-5-(2-fluorophenyl) -3-amino-1-(1-trityl-4-imidazolyl)methyl- 2H-1,4-benzodiazepine -2-one and (3S)-1,3-dihydro-5-(2-fluorophenyl) -3-amino-1-(1-trityl-4-imidazolyl)-methyl-2H-1,4-benzodiazepine -2-one was obtained from the filtrate.

(2) (S)-(+)-Mandelic acid salt of (3S)-1,3-dihydro-5-(2-fluorophenyl) -3-amino-1-(1-trytyl-4-imidazolyl)methyl2H-1,4-benzodiazepine -2-one obtained in Preparation 12(1) was suspended in a mixture of water and ethyl acetate. The resultant mixture was adjusted to pH 7-8 with an aqueous solution of sodium bicarbonate under stirring. The organic layer was separated, washed with water and evaporated to dryness to give (3S)-1,3-dihydro-5-(2-fluorophenyl) -3-amino-1-(1-trityl-4-imidazolyl)methyl2H-1,4-benzodiazepine-2-one (181.4 mg).

$[\alpha]_D^{24} = -35.34°$ (C=0.846, CH$_3$OH)

PREPARATION 13

(1) A mixture ($[\alpha]_D = +14.4°$) (1.57 g) of (3R)-1,3-dihydro-5-(2-fluorophenyl)-3-amino-1-(1-trityl-4-imidazolyl)methyl -2H-1,4-benzodiazepine-2-one and (3S)-1,3-dihydro-5-(2-fluorophenyl)-3-amino-1-(1-trityl-4-imidazolyl)methyl -2H-1,4-benzodiazepine-2-one obtained in Preparation 12(1) was dissolved in a mixture of ethyl acetate (5.3 ml) and methanol (0.5 ml). To a solution was added a solution of (R)—(—)—mandelic acid (342.7 mg) in ethyl acetate (20 ml) under stirring at ambient temperature. To the mixture was added diisopropyl ether (0.5 ml) and the resultant mixture was stirred for 2 hours and allowed to stand overnight. The precipitates were collected by filtration, washed with ethyl acetate and diisopropyl ether and dried to give (R)—(—)—mandelic acid salt of (3R)-1,3-dihydro-5-(2-fluorophenyl)-3-amino-1-(1-trityl-4-imidazolyl)methyl -2H-1,4-benzodiazepine-2-one (white powder, 685.6 mg).

$[\alpha]_D^{24} = +33.60°$ (C=0.848, CH$_3$OH) (2) (3R)-1,3-Dihydro-5-(2-fluorophenyl)-3-amino-1-(1-trityl-4-imidazolyl)methyl -2H-1,4-benzodiazepine-2-one was obtained by treating (R)-(-)-mandelic acid salt of (3R)-1,3-dihydro-5-(2-fluorophenyl)-3-amino-1-(1-trityl-4-imidazolyl)methyl -2H-1,4-benzodiazepine-2-one in a similar manner to that of Preparation 12(2).

$[\alpha]_D^{22} = +37.91°$ (C=0.844, CH$_3$OH)

EXAMPLE 33

The following compounds were obtained according to a similar manner to that of Example 6(1).

(1) (3S)-1,3-Dihydro-1-(1-trityl-4-imidazolyl)methyl-3-(2-indolylcarbonylamino) -5-(2-fluorophenyl)-2H-1,4-benzodiazepine-2-one NMR (CDCl$_3$, δ) : 5.085 (2H, ABq), 5.76 (1H, d, J=7.9Hz), 6.8–8.0 (30H, m), 8.10 (1H, d, J=7.9Hz), 9.81 (1H, s)

(2) (3R)-1,3-Dihydro-1-(1-trityl-4-imidazolyl)methyl-3-(2-indolylcarbonylamino) -5-(2-fluorophenyl)-2H-1,4-benzodiazepine-2-one NMR (DMSO-d$_6$, δ) : 5.11 (2H, ABq), 5.64 (1H, d, J=8.0Hz), 6.7–8.0 (30H, m), 9.55 (1H, d, J=8.0Hz), 11.66 (1H, s)

(3) (3RS)-1,3-Dihydro-3-(2-indolylcarbonylamino)-1-(4-imidazolylmethyl) -5-phenyl-2H-1,4-benzodiazepine-2-one IR (Nujol) : 3250, 1680, 1635, 1600, 1530 cm$^{-1}$ (4) (3RS)-1,3-Dihydro-3-(2-indolylcarbonylamino)-1-(4-imidazolylmethyl) -5-(2-fluorophenyl)-2H-1,4-benzodiazepine-2-one NMR (CDCl$_3$, δ) : 4.85, 5.10 (2H, ABq, J=15Hz), 5.80 (1H, d, J=8Hz), 6.80–7.83 (15H, m), 8.10 (1H, d, J=8Hz), 10.10 (1H, broad s)

(5) (3RS)-1,3-Dihydro-3-(2-indolylcarbonylamino)-1[(5-methylimidazol-4-yl)methyl]-5-phenyl-2H-1,4-benzodiazepine-2-one NMR (DMSO-d$_6$, δ) : 1.96 (3H, s), 4.80, 5.15 (2H, ABq, J=15Hz), 5.55 (1H, d, J=8Hz), 6.90–8.15 (15H, m), 9.33 (1H, d, J=8Hz), 11.58 (2H, br s)

(6) (3S)-1,3-Dihydro-1-(4-imidazolylmethyl)-3-(2-indolylcarbonylamino) -5-(2-fluorophenyl)-2H-1,4-benzodiazepine-2-one NMR (DMSO-d$_6$, δ) : 5.04 (2H, ABq), 5.63 (1H, d, J=7.9Hz), 6.9–8.2 (15H, m), 9.58 (1H, d, J=7.9Hz), 11.65 (1H, s), 11.92 (1H, s)

(7) (3R)-1,3-Dihydro-1-(4-imidazolylmethyl)-3-(2-indolylcarbonylamino) -5-(2-fluorophenyl)-2H-1,4-benzodiazepine-2-one NMR (DMSO-d$_6$, δ) : 5.04 (2H, ABq), 5.62 [1H, d, J=7.9Hz), 6.9–8.3 (15H, m), 9.58 (1H, d, J=7.9Hz), 11.66 (1H, s), 11.93 (1H, s)

(8) (3RS)-1,3-Dihydro-3-(2-indolylcarbonylamino)-1-(2-imidazolylmethyl) -5-phenyl-2H-1,4-benzodiazepine-2-one NMR (DMSO-d$_6$, δ) : 5.10 (2H, s), 5.65 (1H, d, J=8Hz), 6 60–8.10 (16H, m), 9.36 (1H, d, J=8Hz), 11.65 (1H, br s), 11.90 (1H, br s)

(9) (3RS)-1,3-Dihydro-3-(2-indolylcarbonylamino)-1-(3-pyrazolylmethyl) -5-phenyl-2H-1,4-benzodiazepine-2one NMR (DMSO-d$_6$, δ) : 5.03, 5.30 (2H, ABq, J=15Hz), 5.65 (1H, d, J=8Hz), 5.85 (1H, br s), 6.90–7.90 (15H, m), 9.43 (1H, d, J=8Hz), 11.60 (1H, br s), 12.55 (1H, br s)

(10) (3RS)-1,3-Dihydro-3-(2-indolylcarbonylamino)-1-(1,2,4-triazol-3-yl)methyl]-5-phenyl-2H-1,4-benzodiazepine-2-one NMR (DMSO-d$_6$, δ) : 5.10, 5.35 (2H, ABq, J=15Hz), 5.66 (1H, d, J=8Hz), 6.90–7.93 (15H, m), 8.23 (1H, br s), 9.40 (1H, d, J=8Hz), 11.65 (1H, br s)

(11) (3RS)-1,3-Dihydro-3-(2-indolylcarbonylamino)-1-[2-(4-imidazolyl)ethyl]-5-phenyl-2H-1,4- benzodiazepine-2-one NMR (DMSO-d$_6$, δ) : 2.63 (2H, t, J=7Hz), 3.85–4.20 6.60 (1H, s), 6.93–7.85 (15H, m), 9.43 (1H, d, J=8Hz), 11.65 (1H, br s)

(12) (3S)-1,3-Dihydro-1-(4-imidazolylmethyl)-3-(2-indolylcarbonylamino) -5-(2-fluorophenyl)-2H-1,4-benzodiazepine-2-one hydrochloride NMR (DMSO-d$_6$, δ) : 5.33 (2H, ABq), 5.69 (1H, d, J=7.6Hz), 7.0–8.0 (15H, m), 9.05 (1H, s), 9.60 (1H, d, J=7.6Hz), 11.74 (1H, s), 14.73 (1H, broad s)

EXAMPLE 34

A mixture of (3S)-1,3-dihydro-5-(2-fluorophenyl)-3-amino-1-(1-trityl-4-imidazolyl) methyl-2H-1,4-benzodiazepine-2-one (0.79 g), indole-2-carboxylic acid (0.22 g) N-hydroxybenzotriazole (0.18 g) and N,N'-dicyclohexylcarbodiimide (0.28 g) in N,N-dimethylformamide (8 ml) was stirred at ambient temperature overnight and filtered. The filtrate and washings were diluted with ethyl acetate. The mixture was washed with an aqueous solution of sodium bicarbonate. The separated organic layer was washed with water and dried over magnesium sulfate. The solvent was removed under reduced pressure to give a viscous oil (1.12 g), which was chromatographed on silica gel with an eluent of a mixture of chloroform and methanol (30:1) to afford (3S)-1,3-dihydro-1-(1-trityl-4-imidazolyl)methyl -3-(2-indolylcarbonylamino)2-fluorophenyl)-2H-1,4-benzodiazepine-2-one (amorphous substance, 0.97 g).

$[\alpha]_D^{23} = -32.47°$ (C=0.85, CH$_3$OH)

NMR (CDCl$_3$, δ) : 5.085 (2H, ABq), 5.76 (1H, d, J=7.9Hz), 6.8–8.0 (30H, m), 8.10 (1H, d, J=7.9Hz), 9.81 (1H, s)

EXAMPLE 35

To a solution of (3R)-1,3-dihydro-1-(1-trityl-4-imidazolyl)methyl -3-amino-5-(2-fluorophenyl)-2H-1,4-benzodiazepine-2-one (0.81 g), indole-2-carboxylic acid (0.23 g), N-hydroxybenzotriazole (0.19 g) in N,N-dimethylformamide (8 ml) were added 1-ethyl-3-(3-dimethylaminopropyl)carbodiimide hydrochloride (0.27 g) and triethylamine (0.14 g) under stirring at ambient temperature. The mixture was stirred for 4 hours at ambient temperature. To the reaction mixture were added ethyl acetate and water under stirring. The mixture was adjusted to pH 8 with an aqueous sodium bicarbonate. The organic layer was separated and the aqueous layer was extracted with ethyl acetate. The separated organic layer and the extract were combined, washed with water twice and dried over magnesium sulfate. The solvent was removed under reduced pressure to give (3R)-1,3-dihydro-1-(1-trityl-4-imidazolyl)-methyl-3-(2-indolylcarbonylamino) -5-(2-fluorophenyl)-2H-1,4-benzodiazepine-2-one (1.0 g).

$[\alpha]_D^{22} = +41.58°$ (C=0.856, CH$_3$OH)

NMR (DMSO-d$_6$, δ) : 5.11 (2H, ABq), 5.64 (1H, d, J=8.0Hz), 6.7–8.0 (30H, m), 9.55 (1H, d, J=8.0Hz), 11.66 (1H, s)

EXAMPLE 36

To a solution of (3S)-1,3-dihydro-1-(1-trityl-4-imidazolyl)methyl -3-(2-indolylcarbonylamino)-5-(2-fluorophenyl)-2H-1,4-benzodiazepine-2-one (1.0 g) in N,N-dimethylformamide (10 ml) was added 6N hydrochloric acid (7 ml) under stirring and cooling in an ice-bath. The mixture was warmed to 50° C. and stirred for 2 hours. After cooling to room temperature, to the reaction mixture were added water and ethyl acetate under stirring. The mixture was adjusted to pH 8 with an aqueous solution of sodium bicarbonate. The separated organic layer was washed with water and dried. Removal of the solvent gave a viscous oil (1.20 g), which was chromatographed on silica gel with an eluent of a mixture of chloroform and methanol (20:1) to afford (3S)-1,3-dihydro-1-(4-imidazolylmethyl) -3-(2-indolylcarbonylamino)-5-(2-fluorophenyl) -2H-1,4-benzodiazepine-2-one (601.5 mg) as an yellow crystalline powder.

$[\alpha]_D^{20} = +24.68°$ (C=0.64, CHCl$_3$)

NMR (DMSO-d$_6$, δ) : 5.04 (2H, ABq), 5.63 (1H, d, J=7.9Hz), 6.9–8.2 (15H, m), 9.58 (1H, d, J=7 9Hz), 11.65 (1H, s), 11.92 (1H, s)

EXAMPLE 37

The following compound was obtained according to a similar manner to that of Example 36.

(3R)-1,3-Dihydro-1-(4-imidazolylmethyl)-3-(2-indolylcarbonylamino) -5-(2-fluorophenyl)-2H-1,4-benzodiazepine-2-one $[\alpha]_D^{25} = -26.40°$ (C=0.64, CHCl$_3$)

NMR (DMSO-d$_6$, δ) : 5.04 (2H, ABq), 5.62 (1H, d, J=7.9Hz), 6.9–8.3 (15H, m), 9.58 (1H, d, J=7.9Hz), 11.66 (1H, s), 11.93 (1H, s)

EXAMPLE 38

To a solution of (3S)-1,3-dihydro-1-(4-imidazolylmethyl) -3-(2-indolylcarbonylamino)-5-(2-fluorophenyl) -2H-1,4-benzodiazepine-2-one (215.1 mg) in methanol (5 ml) was added 6N-hydrogen chloride solution in ether (0.1 ml) under cooling. The clear yellow solution was evaporated to dryness under reduced pressure. The residue was triturated in ether to afford yellow powder, which was collected by filtration and washed twice with ether to give (3S)-1,3-dihydro-1-(4-imidazolylmethyl)-3-(2-indolylcarbonylamino) -5-(2-fluorophenyl)-2H-1,4-benzodiazepine-2-one hydrochloride (197.1 mg).

$[\alpha]_D^{24} = -35.94°$ (C=0.612, CH$_3$OH)

mp : 214–218° C. (dec.)

NMR (DMSO-d$_6$, δ) : 5.33 (2H, ABq), 5.69 (1H, d, J=7 6Hz), 7.0–8.0 (15H, m), 9.05 (1H, s), 9.60 (1H, d, J=7.6Hz), 11.74 (1H, s), 14.73 (1H, broad s)

EXAMPLE 39

To a solution of (3S)-1,3-dihydro-1-(4-imidazolylmethyl) -3-(2-indolylcarbonylamino)-5-(2-fluorophenyl) -2H-1,4-benzodiazepine-2-one (246 mg) in methanol (10 ml) was added L-(+)-tartaric acid (75.0 mg) at room temperature. After being stirred for several minutes, the mixture was concentrated to 2 ml. The resultant light yellow powder was collected by filtration, washed with diisopropyl ether twice and dried to give (3S)-1,3-dihydro-1-(4-imidazolylmethyl)-3-(2-indolylcarbonylamino) -5-(2-fluorophenyl)-2H-1,4-benzodiazepine-2-one L-(+)-tartrate (235.3 mg).

mp : 170–175° C. (dec.)

NMR (DMSO-d$_6$, δ) : 4.31 (2H, s), 5.07 (2H, s), 5.63 (1H, d, J=7.7Hz), 6.9–8.1 (15H, m), 9.58 (1H, d, J=7.7Hz), 11.65 (1H, s)

EXAMPLE 40

The following compound was obtained by reacting (3S)-1,3-dihydro-1-(4-imidazolylmethyl)-3-(2-indolylcarbonylamino) -5-(2-fluorophenyl)-2H-1,4-benzodiazepine-2-one with methanesulfonic acid in similar manners to those of Examples 38 and 39.

(3S)-1,3-Dihydro-1-(4-imidazolylmethyl)-3-(2-indolylcarbonylamino) -5-(2-fluorophenyl)-2H-1,4-benzodiazepine-2-one methanesulfonate $[\alpha]_D^{24} = -31.32°$ (C=0.632, CH$_3$OH)

mp : 136–139° . (dec.)

NMR (DMSO-d$_6$, δ) : 2.39 (3H), 5.33 (2H, ABq), 5.69 (1H, d, J=7.7Hz), 7.0–7.8 (15H, m), 8.99 (1H, s), 9.58 (1H, d, J=7.7Hz), 11.68 (1H, s), 14.26 (1H, broad)

EXAMPLE 41

The following compounds were obtained according to a similar manner to that of Example 4(1).

(1) (3RS)-1,3-Dihydro-3-(2-indolylcarbonylamino)-1-(4-imidazolylmethyl) -5-phenyl-2H-1,4-pine-2-one IR (Nujol) : 3250, 1680, 1635, 1600, 1530 cm$^{-1}$ (2) (3RS)-1,3-Dihydro-3-(2-indolylcarbonylamino)-1-(4-imidazolylmethyl) -5-(2-fluorophenyl)-2H-1,4-benzodiazepine-2-one NMR (CDCl$_3$, δ) : 4.85, 5.10 (2H, ABq, J=15Hz), 5 5.80 (1H, d, J=8Hz), 6.80–7.83 (15H, m), 8.10 (1H, d, J=8Hz), 10.10 (1H, broad s)

(3) (3RS)-1,3-Dihydro-3-(2-indolylcarbonylamino)-1-[(5-methylimidazol-4-yl)methyl]-5-phenyl-2H-1,4benzodiazepine-2-one NMR (DMSO-d6, δ) : 1.96 (3H, s), 4.80, 5.15 (2H, ABq, J=15Hz), 5.55 (1H, d, J=8Hz), 6.90–8.15 (15H, m), 9.33 (1H, d, J=8Hz), 11.58 (2H, br s)

(4) (3S)-1,3-Dihydro-1-(4-imidazolylmethyl)-3-(2-indolylcarbonylamino) -5-(2-fluorophenyl)-2H-1,4-benzodiazepine-2-one NMR (DMSO-d6, δ) : 5.04 (2H, ABq), 5.63 (1H, d, J=7 9Hz), 6.9–8.2 (15H, m), 9.58 (1H, d, J=7.9Hz), 11.65 (1H, s), 11.92 (1H, s)

(5) (3R)-1,3-Dihydro-1-(4-imidazolylmethyl)-3-(2-indolylcarbonylamino) -5-(2-fluorophenyl)-2H-1,4-benzodiazepine-2-one NMR (DMSO-d6, δ) : 5.04 (2H, ABq), 5.62 (1H, d, J=7.9Hz), 6.9–8.3 (15H, m), 9.58 (1H, d, J=7.9Hz), 11.66 (1H, s), 11.93 (1H., s)

(6) (3RS)-1,3-Dihydro-3-(2-indolylcarbonylamino)-1-(2-imidazolylmethyl) -5-phenyl-2H-1,4-benzodiazepine-2-one NMR (DMSO-d6, δ) : 5.10 (2H, s), 5.65 (1H, d, J=8Hz), 6.60–8.10 (16H, m), 9.36 (1H, d, J=8Hz), 11.65 (1H, br s), 11.90 (1H, br s)

(7) (3RS)-1,3-Dihydro-3-(2-indolylcarbonylamino)-1-(3-pyrazolylmethyl) -5-phenyl-2H-1,4-benzodiazepine-2-one NMR (DMSO-d6, δ) : 5.03, 5.30 (2H, ABq, J=15Hz), 5.65 (1H, d, J=8Hz), 5.85 (1H, br s), 6.90–7.90 (15H, m), 9.43 (1H, d, J=8Hz), 11.60 (1H, br s), 12.55 (1H, br s)

(8) (3RS)-1,3-Dihydro-3-(2-indolylcarbonylamino)-1-[(1,2,4-triazol-3-yl)methyl]-5-phenyl-2H-1,4-benzodiazepine-2-one NMR (DMSO-d6, δ) : 5.10, 5.35 (2H, ABq, J=15Hz), 5.66 (1H, d, J=8Hz), 6.90–7.93 (15H, m), 8.23 [1H, br s), 9.40 (1H, d, J=8Hz), 11.65 (1H, br s)

(9) (3RS)-1,3-Dihydro.-3-(2-indolylcarbonylamino)-1-[2-(4-imidazolyl)ethyl]-5-phenyl-2H-1,4-benzodiazepine-2-one NMR (DMSO-d6, δ) : 2.63 (2H, t, J=7Hz), 3.85–4.20 (1H, m), 4.20–4.75 (1H, m), 5.55 (1H, d, J=8Hz), 6.60 (1H, s), 6.93–7.85 (15H, m), 9.43 (1H, d, J=8Hz), 11.65 (1H, br s)

(10) (3S)-1,3-Dihydro-1-(4-imidazolylmethyl)-3-(2-indolylcarbonylamino) -5-(2-fluorophenyl)-2H-1,4-benzodiazepine-2-one hydrochloride NMR (DMSO-d6, δ) : 5.33 (2H, ABq), 5.69 (1H, d, J=7.6Hz), 7.0–8.0 (15H, m), 9.05 (1H, s), 9.60 (1H, d, J=7.6Hz), 11.74 (1H, s), 14.73 (1H, broad s)

What we claim is:

1. A compound of the formula:

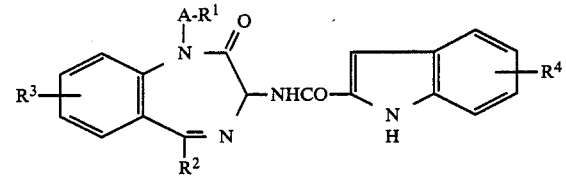

wherein
R$^1$ is tetrazolyl; imidozolyl which may have a lower alkyl and/or a trityl group; or —O—R$^7$ in which R$^7$ is hydrogen or lower alkyl,
R$^2$ is phenyl which may have a halogen atom,
R$^3$ is hydrogen or halogen,
R$^4$ is hydrogen, halogen or lower alkoxy and
A is lower alkylene,
or a pharmaceutically acceptable salt thereof.

2. A compound of claim 1, wherein
R$^1$ is imidazolyl which may have a lower alkyl group,
R$^3$ is hydrogen,
R$^4$ is hydrogen, and
A is C$_1$-C$_3$ alkylene.

3. A compound of claim 2, which is (3S)-1,3-dihydro-1-(4-imidazolylmethyl)-3-(2-indolylcarbonylamino) -5-(2-fluorophenyl)-2H-1,4-benzodiazepine-2-one.

4. A cholecystokinin-antagonist pharmaceutical composition which comprises, as an active ingredient, an effective amount of a compound of claim 1 or a pharmaceutically acceptable salt thereof in admixture with a pharmaceutically acceptable carrier.

5. A method for treating or preventing emesis or pancreatitis which comprises administering an effective amount of a compound of claim 1 or a pharmaceutically acceptable salt thereof to a human or animal.

* * * * *